United States Patent
Ueda et al.

(10) Patent No.: US 9,581,608 B2
(45) Date of Patent: Feb. 28, 2017

(54) SAMPLE ANALYZER AND METHOD FOR CONTROLLING SAMPLE ANALYZER

(71) Applicant: SYSMEX CORPORATION, Kobe-shi, Hyogo (JP)

(72) Inventors: Makoto Ueda, Hyogo (JP); Yuji Wakamiya, Kushiro (JP); Toshikatsu Fukuju, Akashi (JP); Kazunori Mototsu, Kobe (JP)

(73) Assignee: Sysmex Corporation, Hyogo (JP)

( * ) Notice: Subject to any disclaimer, the term of this patent is extended or adjusted under 35 U.S.C. 154(b) by 354 days.

(21) Appl. No.: 13/629,000

(22) Filed: Sep. 27, 2012

(65) Prior Publication Data

US 2013/0078617 A1   Mar. 28, 2013

(30) Foreign Application Priority Data

Sep. 28, 2011   (JP) ................. 2011-212900

(51) Int. Cl.
| | |
|---|---|
| *G01N 33/566* | (2006.01) |
| *C12Q 1/70* | (2006.01) |
| *C12M 1/34* | (2006.01) |
| *G01N 33/50* | (2006.01) |
| *G01N 35/00* | (2006.01) |
| *G01N 35/02* | (2006.01) |
| *G01N 35/04* | (2006.01) |

(52) U.S. Cl.
CPC ..... *G01N 35/00623* (2013.01); *G01N 35/026* (2013.01); *G01N 2035/0415* (2013.01)

(58) Field of Classification Search
USPC ............................................. 422/65; 436/47
See application file for complete search history.

(56) References Cited

U.S. PATENT DOCUMENTS

| | | | | |
|---|---|---|---|---|
| 5,013,529 | A * | 5/1991 | Itoh ................. | 422/511 |
| 7,842,237 | B1 * | 11/2010 | Shibuya et al. ......... | 422/64 |
| 2008/0206100 | A1 | 8/2008 | Matsubara | |
| 2010/0166606 | A1* | 7/2010 | Koike et al. ........... | 422/65 |

FOREIGN PATENT DOCUMENTS

| | | |
|---|---|---|
| JP | 4-65676 A | 3/1992 |
| JP | 2003-329693 A | 11/2003 |
| JP | 2008-064680 A | 3/2008 |
| JP | 2011-117776 A | 6/2011 |

* cited by examiner

*Primary Examiner* — Jill Warden
*Assistant Examiner* — Julie Tavares
(74) *Attorney, Agent, or Firm* — Sughrue Mion, PLLC

(57) ABSTRACT

A sample analyzer transports a first rack and a second rack, the first rack including a first number of supporters for supporting containers that contain biological samples of subjects, and the second rack including a second number of supporters for supporting containers that contain standard samples. The sample analyzer determines whether a transport object is the first rack or the second rack. When it has been determined that the transport object is the second rack, the sample analyzer performs a transporting operation according to the second rack and measure the standard samples in the containers supported by the second rack in a predetermined order, and prepares a calibration curve used for analyzing a measurement result of a biological sample, based on a plurality of measurement results of the standard samples.

16 Claims, 15 Drawing Sheets

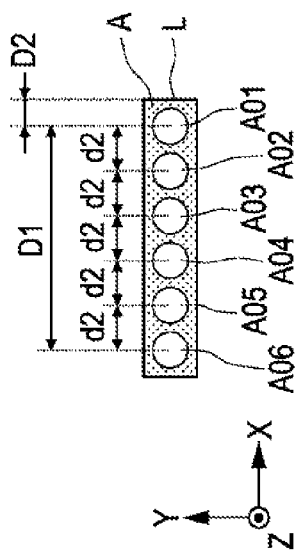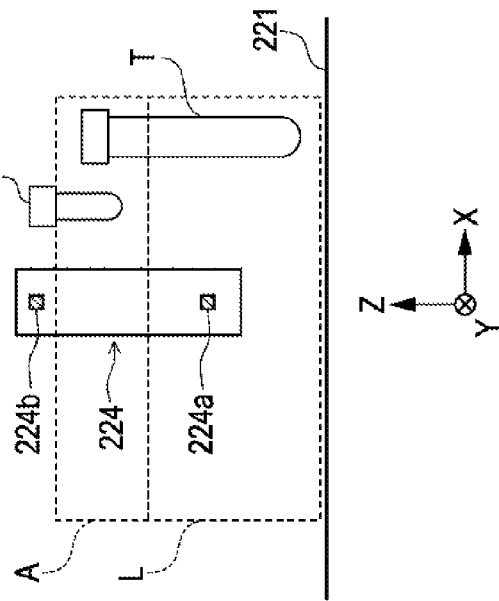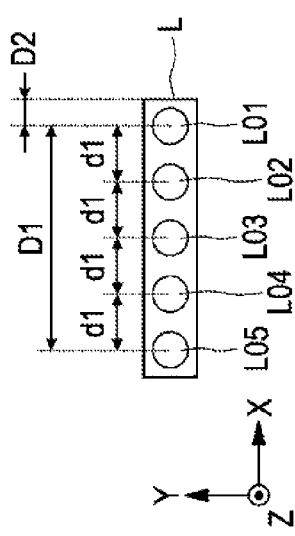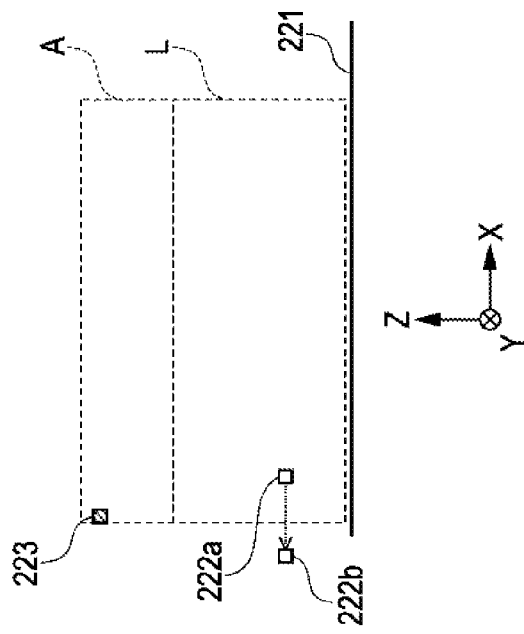

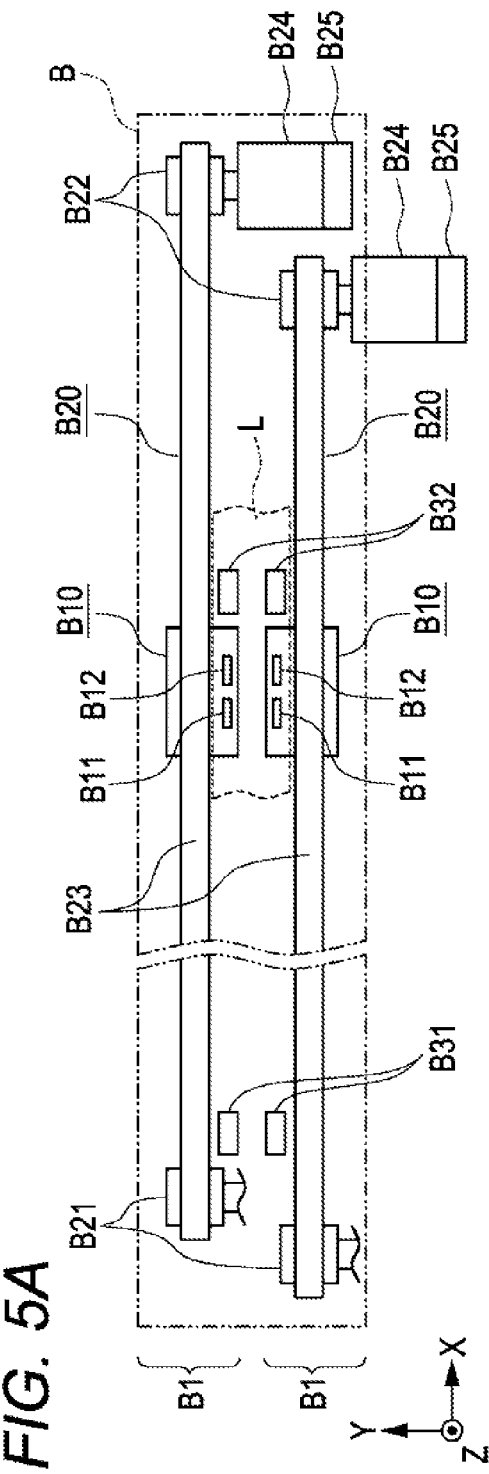
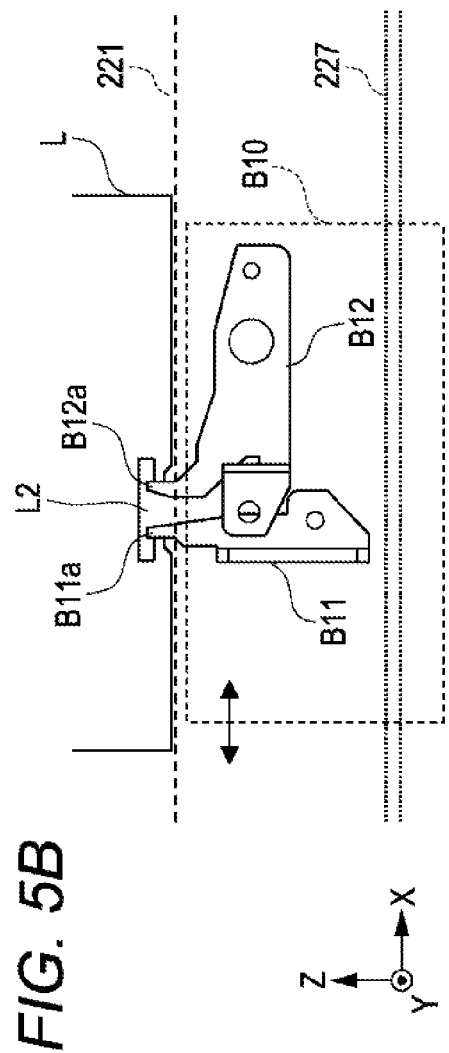

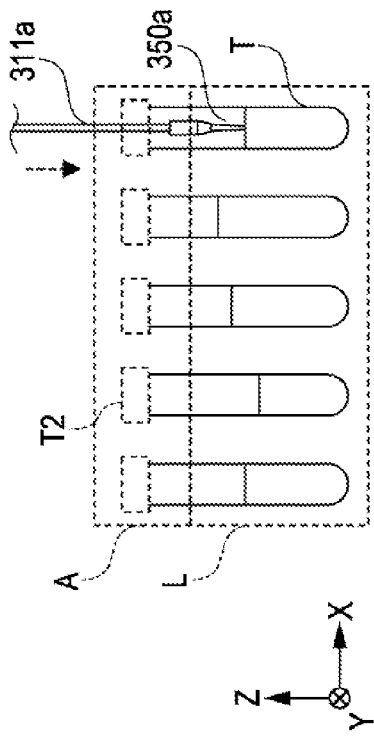
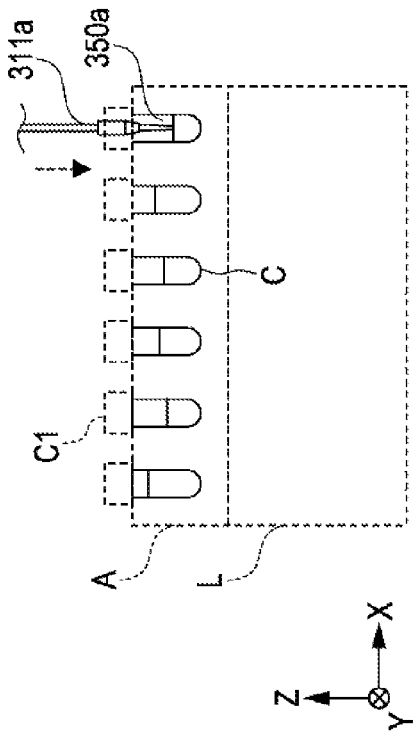
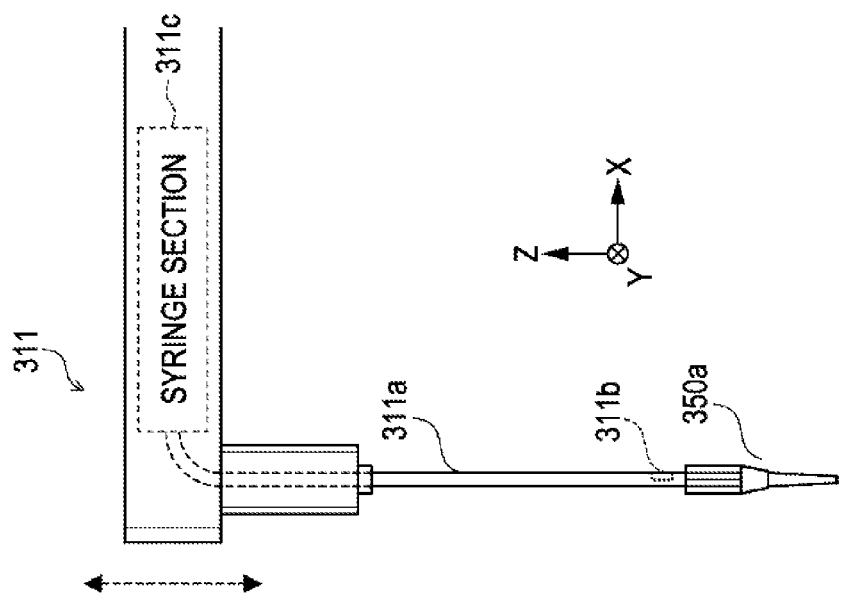

| SAMPLE | CONCENTRATION | | COUNT | CALCULATED VALUE | CV[%] |
|---|---|---|---|---|---|
| C0 | 0.000 | | 881 | 0.010 | 10.00 |
| C1 | 0.250 | C | 14406 | 0.260 | 5.00 |
| C2 | 2.500 | C | 151937 | 2.600 | 2.00 |
| C3 | 25.000 | | 1296400 | 26.000 | 1.00 |
| C4 | 250.000 | | 10880800 | 260.000 | 0.50 |
| C5 | 2500.000 | | 59133200 | 26000.000 | 0.10 |

ID 12345
Calibration 2011/03/31 23:59
Validation: Not Validate
Exp Date 2011/09/01

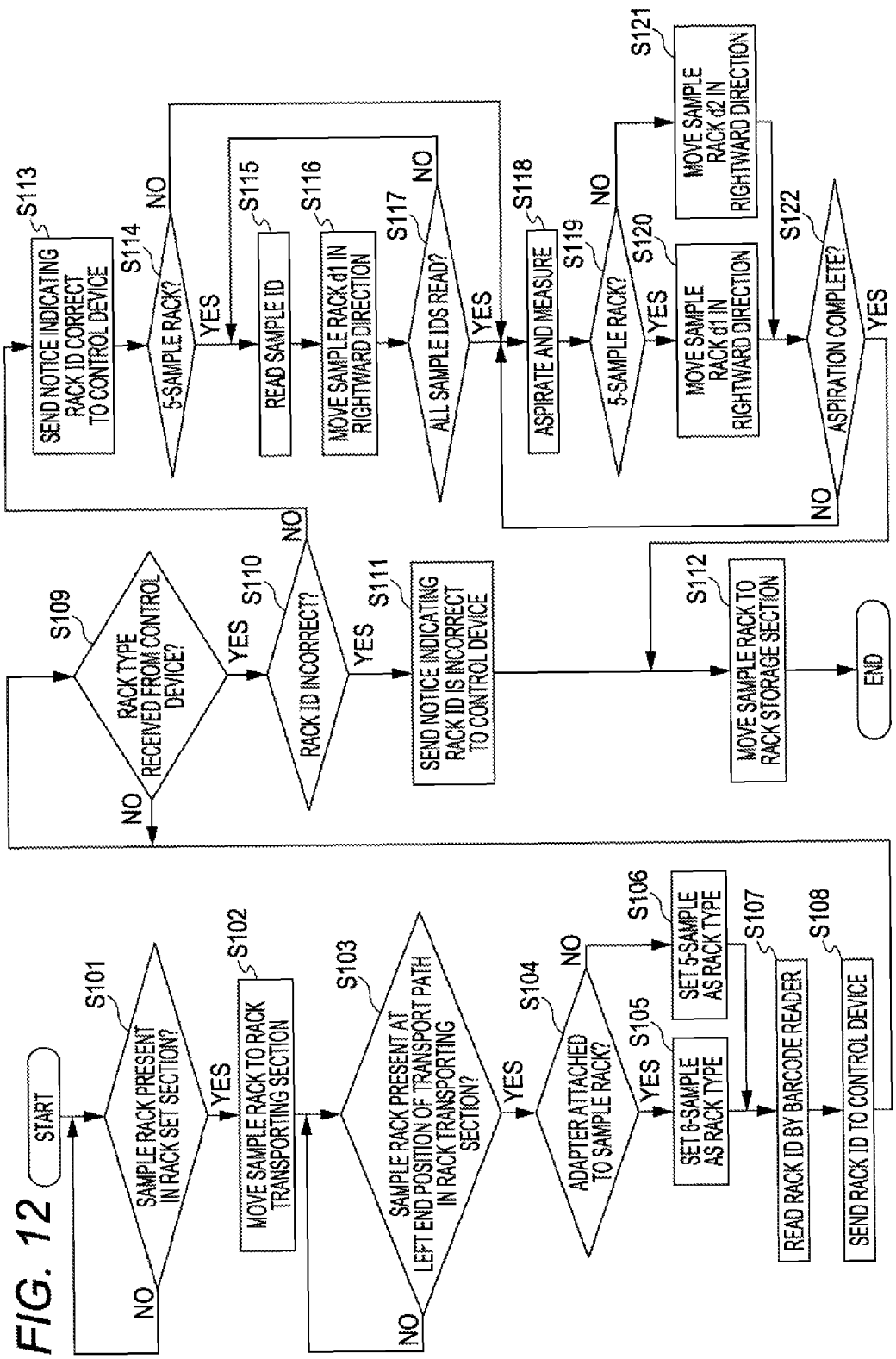

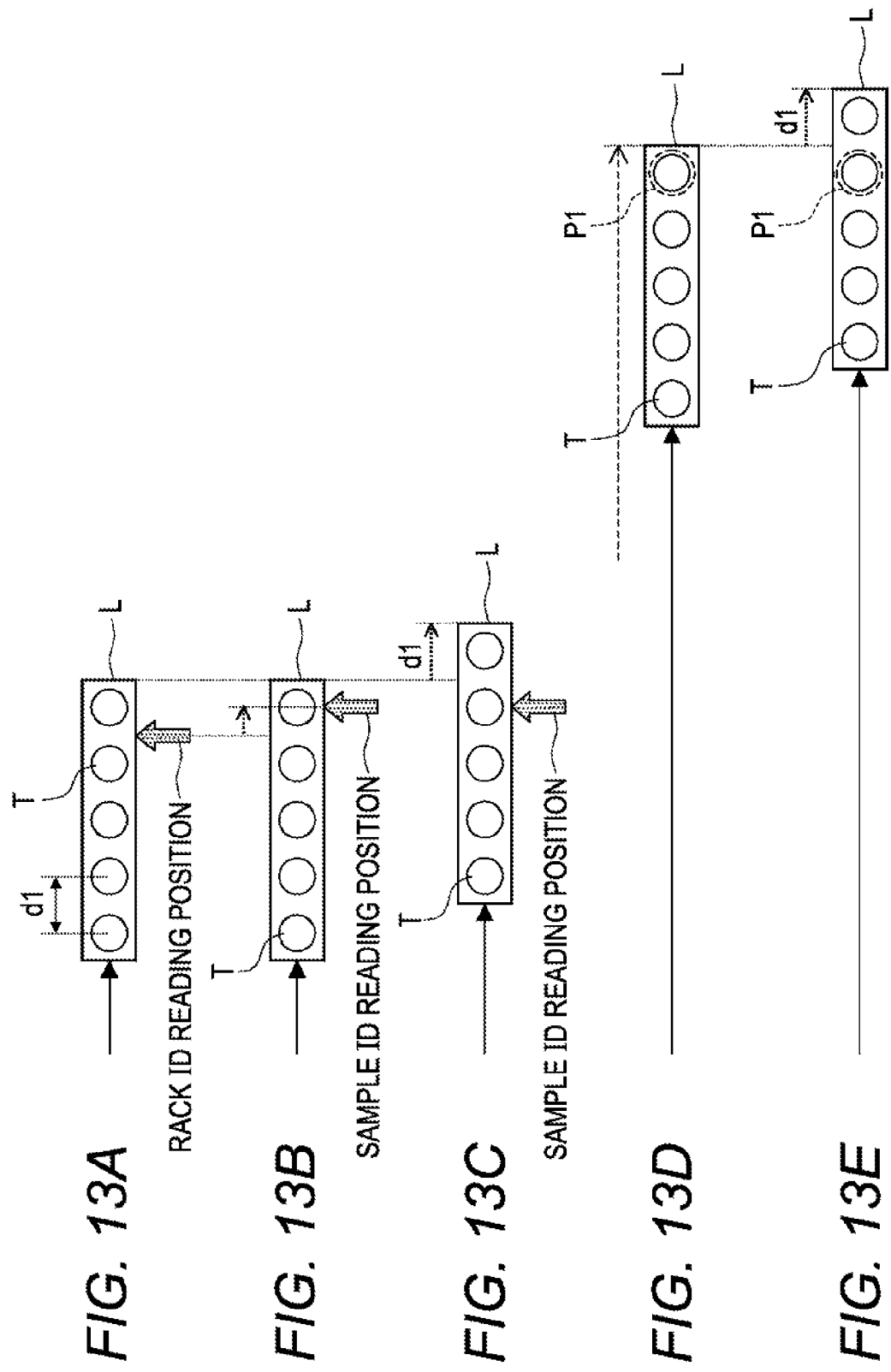

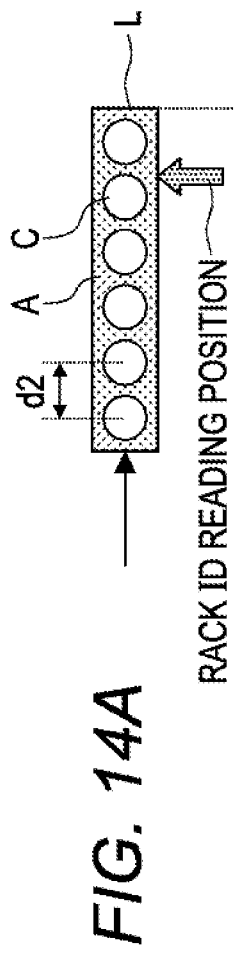
FIG. 14A
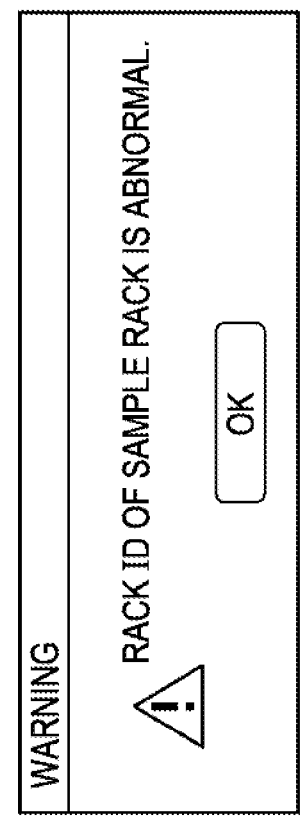
FIG. 14B
FIG. 14C
FIG. 14D

SAMPLE ANALYZER AND METHOD FOR CONTROLLING SAMPLE ANALYZER

FIELD OF THE INVENTION

The present invention relates to a sample analyzer for performing measurements by operating a processing unit, and a method of controlling the sample analyzer.

BACKGROUND

For example, Japanese Laid-Open Patent Publication No. 2008-64680 discloses a conventional sample analyzer for transporting a sample rack holding a plurality of sample containers, and analyzing the samples in the sample containers.

Japanese Laid-Open Patent Publication No. 2008-64680 discloses an automatic analyzer which transports a sample rack via a sampler, and measures a standard sample held in the sample rack. This automatic analyzer processes the data of the standard samples and prepares a calibration curve.

When measuring the standard sample and preparing the calibration curve, a plurality of standard samples are usually held in the sample rack according to the order of their concentration, and measurements are performed in the sequence of the concentrations as in the automatic analyzer disclosed in Japanese Laid-Open Patent Publication No. 2008-64680. During this measurement, it is sometimes necessary to measure more standard samples than can be held in a single sample rack. When containers accommodating standard samples are held in a plurality of sample racks, there is concern that the user may mistake about the order of the positions of the sample racks in the sampler. In this case, the order in which the standard samples are measured may not be correct, resulting in concern that an accurate calibration curve cannot be prepared.

When measuring standard samples that number fewer than the number of container supporters of a single sample rack, however, the containers accommodating the standard samples may be placed non-continuously in the sample rack so as to have empty space therebetween. In this case, aspiration abnormalities may occur when sample cannot be aspirated from a container supporter that does not hold a standard sample, and a calibration curve cannot be properly prepared. There is also concern of increasing complexity of the controls related to the measurements in order to properly measure the standard samples.

SUMMARY

The scope of the present invention is defined solely by the appended claims, and is not affected to any degree by the statements within this summary.

A first aspect of the present invention is a sample analyzer, comprising: a transporting section configured to transport a first rack which includes a first number of supporters for supporting containers that contain biological samples of subjects, and configured to transport a second rack which includes a second number of supporters for supporting containers that contain standard samples, wherein the second number is different from the first number; a measurement section configured to measure a sample in a container transported by the transporting section, and a controller configured to determine whether a rack transported by the transporting section is the first rack or the second rack; when it has been determined that the rack transported by the transporting section is the second rack, control the transporting section to perform a transporting operation according to the second rack and control the measurement section to measure the standard samples in the containers supported by the second rack in a predetermined order; and prepare a calibration curve used for analyzing a measurement result of a biological sample, based on a plurality of measurement results of the standard samples.

A second aspect of the present invention is a method for controlling a sample analyzer that comprises a transporting section for transporting a rack and a measurement section for measuring a sample in a container supported by the rack, the method comprising steps of: determining whether a transport object of the transporting section is a first rack which includes a first number of supporters for supporting containers that contain biological samples of subjects, or a second rack which includes a second number of supporters for supporting containers that contain standard samples, wherein the second number is different from the first number; controlling the transporting section to perform a transport operation according to the second rack when the transport object has been determined to be the second rack; controlling the measurement section to measure, in a predetermined order, the standard samples in the containers supported by the second rack transported by the transporting section; and preparing a calibration curve used in an analysis of a measurement result of a biological sample based on a plurality of measurement results of the standard samples in the containers supported by the second rack.

BRIEF DESCRIPTION OF THE DRAWINGS

FIGS. 4(a) through 4(d) are plan views showing the structures of the embodiment of the sample rack and sample rack with the attached adapter viewed from the side, and a side view of the sensor position;

FIGS. 5(a) and 5(b) are a plan view showing the structure of the moving mechanism of the embodiment, and a side view showing the essential part of the connection unit;

FIG. 7(a) is a side view showing the vicinity of the pipette on the sample dispensing arm of the embodiment, and FIGS. 7(b) and 7(c) are side views showing the condition when liquid surface detection is performed;

FIG. 10 shows the calibration curve rack setting screen of the embodiment;

FIG. 11 shows the calibration curve screen of the embodiment;

FIG. 12 is a flow chart showing the processing performed by the CPU of the measurement section of the embodiment;

FIGS. 13(a) through 13(e) illustrate the transport of the sample rack of the embodiment;

FIGS. 14(a) through 14(d) illustrate the transport of the sample rack with the mounted adapter of the embodiment, and the rack ID abnormality screen of the embodiment.

DETAILED DESCRIPTION OF THE EMBODIMENT

Figure 1:
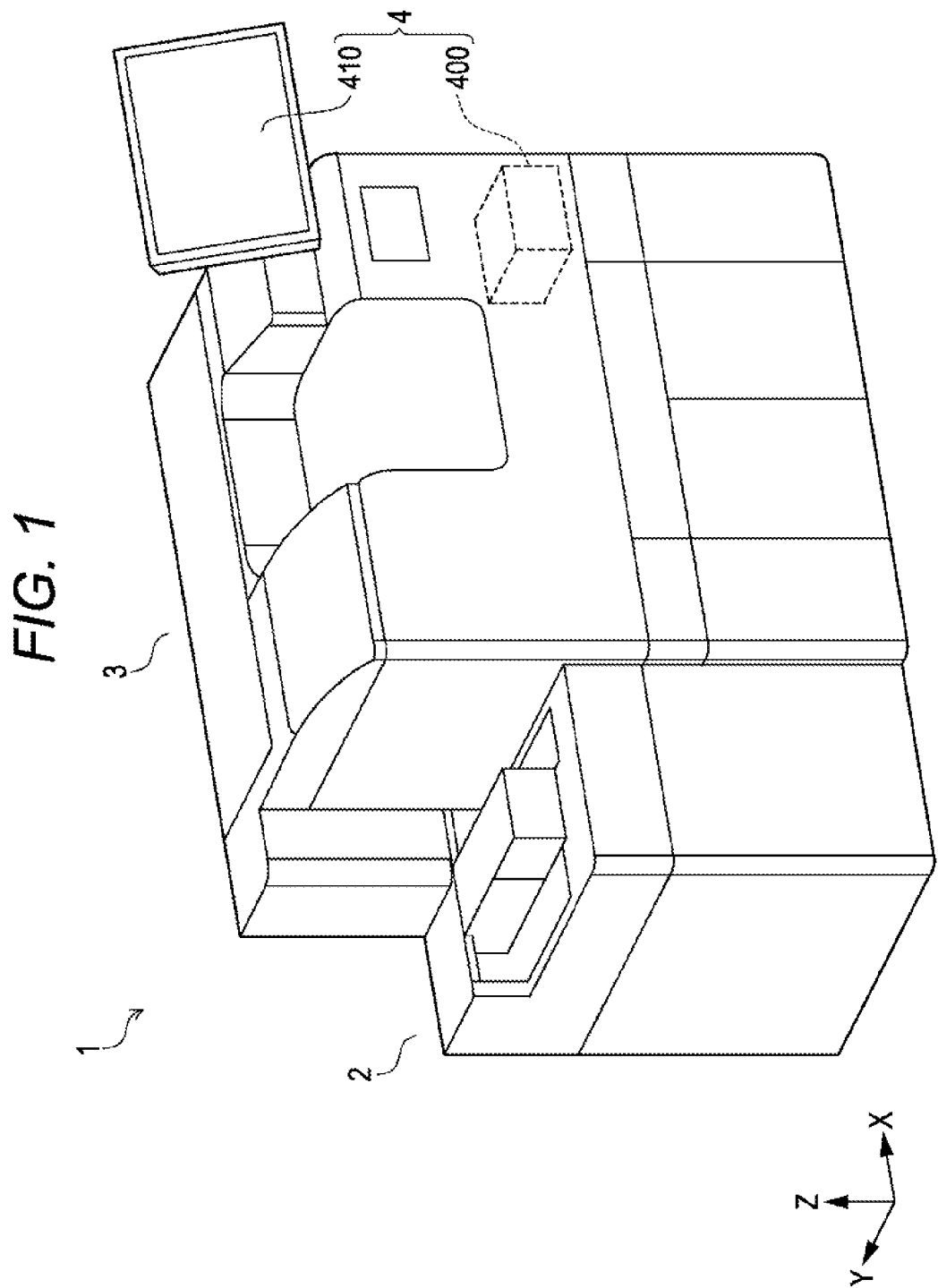
FIG. 1 is a perspective view showing the general structure of an embodiment of an immunoanalyzer.

An embodiment of the present invention applies the present invention to an immunoanalyzer for examining various items such as hepatitis B, hepatitis C, tumor markers, and thyroid hormone using a sample such as blood.

The immunoanalyzer of the embodiment is described below referring to the drawings.

FIG. 1 is a perspective view showing the general structure of an immunoanalyzer 1. The immunoanalyzer 1 has a sample transporting section (sampler) 2, measurement section 3, and control device 4.

The sample transporting section 2 is configured to move the sample rack L which holds sample containers T that contain samples. The structures of the sample container T and sample rack L are described below referring to FIGS. 3(a) and (b). The measuring section 3 measures a sample aspirated from the sample container T transported by the sample transporting section 2 to a predetermined position. The measurement data of the sample measured by the measurement section 3 are converted using a calibration curve previously prepared by measuring standard samples of known concentrations (calibrators). Analysis results of this sample are thus obtained. The control device 4 has a main body 400, and a display/input section 410 configured by a touch panel; the control device 4 controls the sample transporting section 2 and the measurement section 3 when instructions are received from a user.

Figure 2:
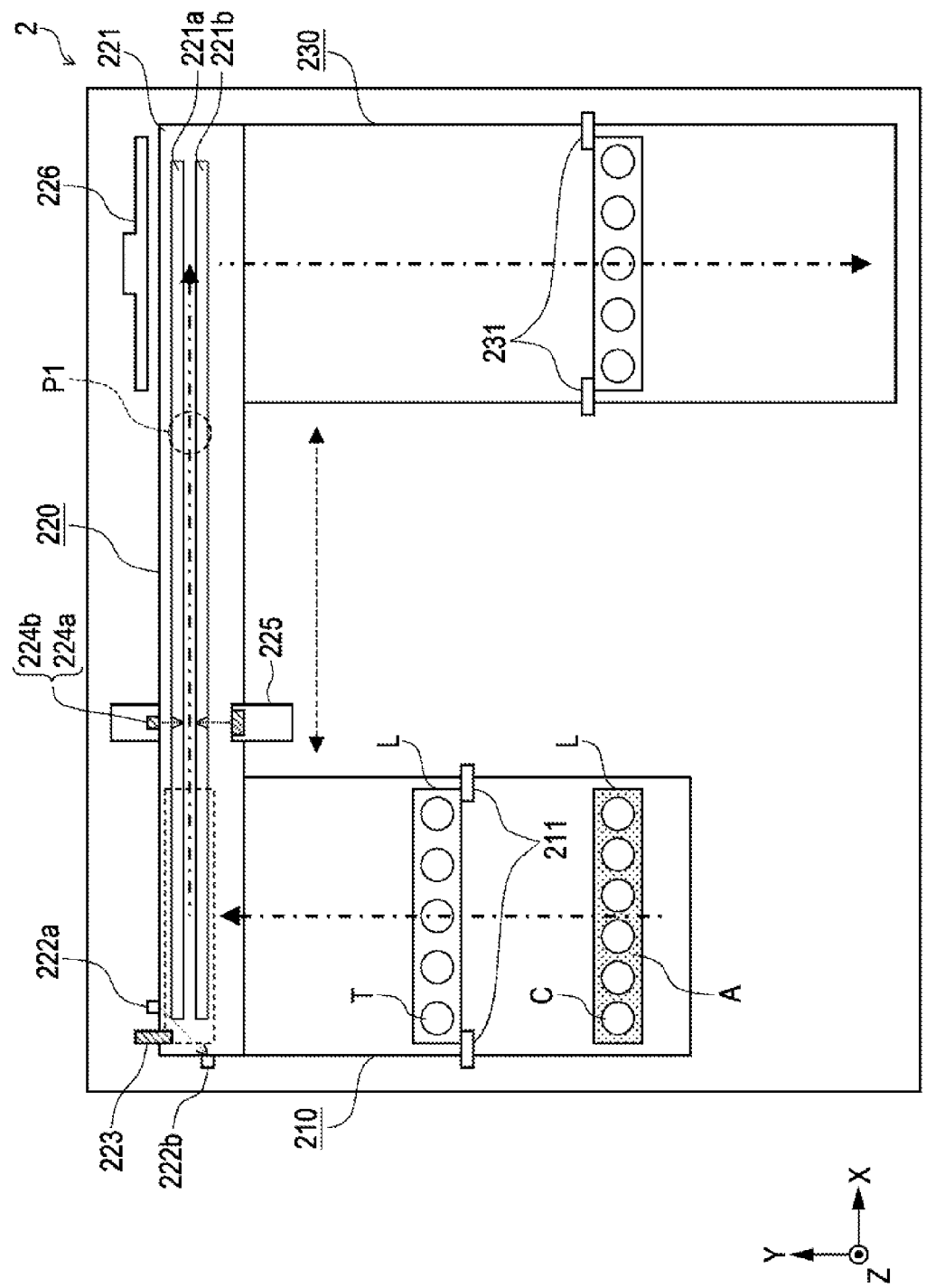
FIG. 2 is a plan view showing the structure of the sample transporting section of the embodiment viewed from above.

FIG. 2 is a plan view showing the structure when viewing the transporting section 2 from above.

The sample transporting section 2 has a rack set part 210, rack transport part 220, and rack storage part 230. The rack set part 210, rack transport part 220, and rack storage part 230 are configured to move the sample rack L capable of holding five sample containers T along the dot-dash arrow line. The rack set part 210, rack transport part 220, and rack storage part 230 of the present embodiment are also configured to similarly move a sample rack L capable of holding six sample cups C by attaching an adapter A.

Figure 3A:
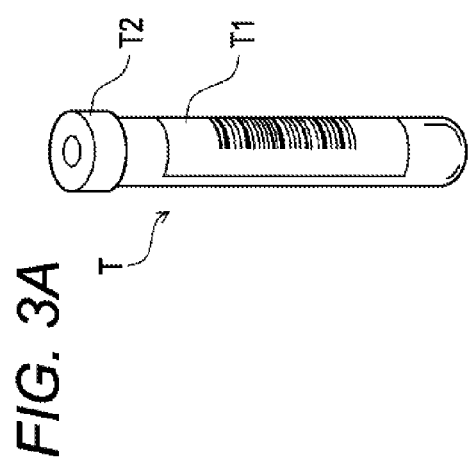
FIGS. 3(a) through 3(d) show the structures of the embodiment of the sample container, sample rack, sample cup, and sample rack with the attached adapter.

FIGS. 3(a) and (b) respectively show the structures of the sample container T and the sample rack L.

Referring to FIG. 3(a), the sample container T is a tube-like container, open at the top end, formed of transparent synthetic resin or glass. A barcode label T1 is adhered to the side surface of the sample container T. A barcode indicating the sample ID is printed on the barcode label T1. The sample container T contains a blood sample collected from a patient, and the opening at the top end is sealed with a cap T2.

Figure 3B:
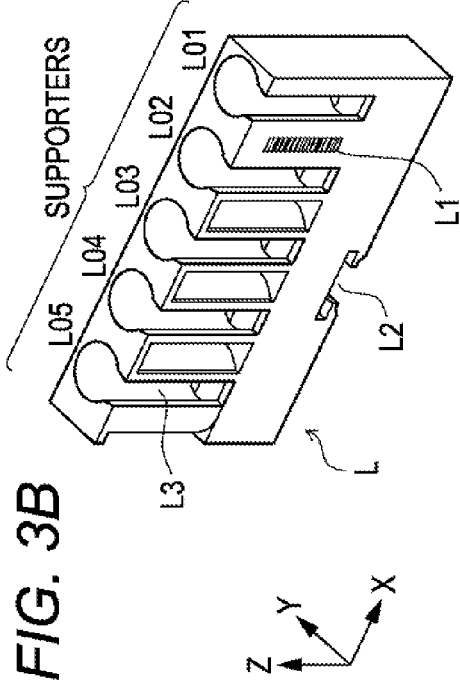

Referring to FIG. 3(b), supporters L01 through L05 are formed on the sample rack L, and are capable of holding five sample containers T in a perpendicular position. A barcode label L1 is adhered to the front side (the surface on the side in the Y-axis negative direction) of the sample rack L. A barcode indicating the rack ID is printed on the barcode label L1. A concavity L2 is formed on the bottom surface of the sample rack L. The concavity L2 is shaped to engage the engaging hooks B11a and B12a arranged below the rack transporting section 220 (described later).

Note that five open parts L3 are formed on the front surface of the sample rack L, and correspond to the positions of the supporter L01 through L05. Similarly, five open parts are formed on the rear surface of the sample rack L, and correspond to the positions of the supporter L01 through L05.

Figure 3C:
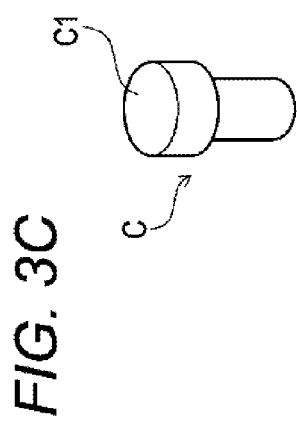

FIGS. 3(c) and (d) respectively show the construction of the sample cup C and the sample rack L with the attached adapter A.

Referring to FIG. 3(c), the sample cup C contains a standard sample for preparing a calibration curve, and is sealed by a cap C1. Note that a barcode label is not adhered to the sample cup C.

Figure 3D:
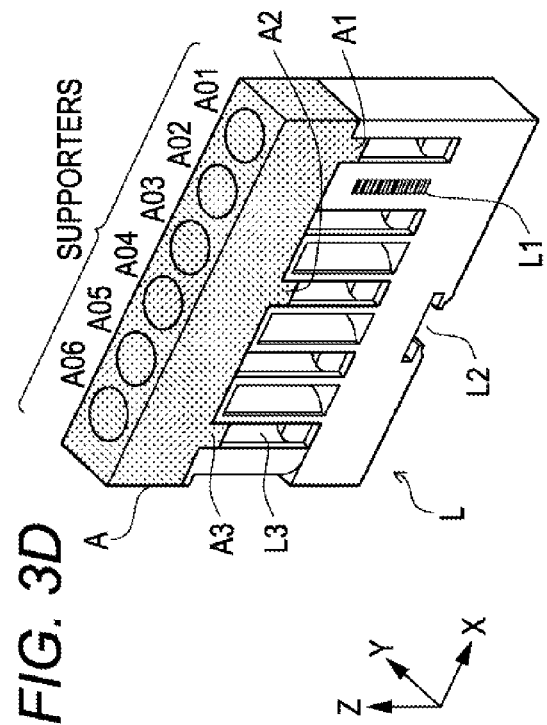

Referring to FIG. 3(d), the width of the adapter A in the longitudinal direction and the latitudinal direction (width in the X axis direction and Y axis direction) is identical to the sample rack L. The adapter A has supporters A01 through A06 for holding six sample cups C perpendicularly. Flange parts A1 through A3 are formed at the bottom end of the adapter A at positions corresponding to the supporters L01, L03, and L05 of the sample rack L. The adapter A is attached to the sample rack L as shown in FIG. 3(d) by fitting the flange parts A1 through A3 on the supporters L01, L03, and L05 from above relative to the sample rack L in the condition shown in FIG. 3(b).

Thus, when the adapter A with the six supporters is attached to the sample rack L which has only five supporters, the sample rack L is then capable of holding six sample cups C. Note that when the sample cups C are held by the supporters A01 through A06, the bottom end of the sample cup C is positioned more to the top side of the bottom surface of the adapter A. Hence, sample cups C can be held in accordance with the number of supporters of the adapter A regardless of the number of supporters of the sample rack L. Note that the adapter A holds six standard sample in the order of their concentrations with the lowest concentration standard sample at the head.

FIGS. 4(a) and (b) are plan views respectively showing the sample rack L and the sample rack L with the attached adapter as viewed from above.

Referring to FIG. 4(a), in the sample rack L, the distance between the center of the supporter L01 on the right end and the center of the supporter L05 on the left end is designated D1, and the center of the supporter L01 on the right end is only a distance D2 from the right side surface. The distance between the centers of the supporters L01 through L05 is designated d1. Referring to FIG. 4(b), similar to the sample rack L, the distance between the center of the supporter A01 on the right end and the center of the supporter A06 on the left end is D1, and the center of the supporter A01 on the right end is only the distance D2 from the right side surface. The distance between the centers of the supporters A01 through A06 is d2, which is less than d1.

Returning now to FIG. 2, when the sample rack L or the sample rack L with the attached adapter A is placed in the rack set part 210, the sample rack is detected by a sensor disposed in the rack set part 210. Thereafter, the front surface of the sample rack L is pushed backward (Y axis positive direction) by a rack moving device 211 until the sample rack L is disposed at the left end position on the transport path 221 of the rack transporting section 220.

Transmission type sensors 222a and 222b, and lever type sensor 223 are arranged in the vicinity of the left end of the rack transporting section 220. As shown in FIG. 4(c), the sensors 222a and 222b are arranged between the top surface and bottom surface of the sample rack L in an upward direction (Z axis direction), and the sensor 223 is disposed between the top surface and the bottom surface of the adapter A attached to the sample rack L.

The sample rack L disposed at the left end position on the transport path 221 from the rack set part 210 is detected by the sensors 222a and 222b. When the adapter A is attached to the sample rack L disposed at the left end position of the transport path 221, the sensor 223 is pushed in the Y axis positive direction by the side surface of the adapter A. Hence, the adapter A attached to the sample rack L is detected.

A moving device B for moving the sample rack L laterally (X axis directions) is disposed below the transport path 221 of the rack transporting section 220. The sample rack L disposed at the left end position on the transport path 221 is moved in the right direction on the transport path 221 by the moving device B.

Reflective sensors 224a and 224b are arranged near the center of the rack transporting section 220. Sensors 224a and 224b are disposed at different positions in vertical directions (Z axis directions) as shown in FIG. 4(d). FIG. 4(d) shows the positions in vertical directions when both the sample container T and sample cup C are being supported. The sensor 224a is positioned at a height corresponding to the opening on the side surface (surface on the side in the Y axis positive direction) at the rear of the sample rack L; the sensor 224b is positioned at a height corresponding to the cap C1 of the sample cup C when the sample cup C is held in the adapter A attached to the sample rack L.

When the supporters of the sample rack L are positioned on the front surface (the side in the Y axis negative direction) of the sensor 224a, the sensor 224a detects whether a sample container T is held by this supporter through the opening on the side surface (the surface on the side in the Y axis negative direction) at the rear of the sample rack L. When the supporters of the adapter A are positioned on the front surface of the sensor 224b, the sensor 224b detects whether a sample cup C is held by this supporter.

A barcode reader 225 is also provided near the center of the rack transporting section 220. The barcode reader 225 is movable in lateral directions near the center of the rack transporting section 220. When the barcode label L1 on the sample rack L is positioned on the front side (the side in the Y axis positive direction) of the barcode reader 225, the barcode reader 225 reads the rack ID from the barcode L1. When the barcode reader 225 is moved laterally and positioned on the front side (side in the R axis negative direction) of the sample container T, the barcode reader 225 then reads the sample ID from the barcode label T1 of the sample container T.

An aspiration position P1 is set near the center of the rack transporting section 220 for the aspiration of the standard sample in the sample cup C and the aspiration of the sample in the sample container T by the measurement section 3. When the sample container T or the sample cup C which is the aspiration object is disposed at the aspiration position P1, the sample dispensing arm 311 of the measurement section 3 (described later) aspirates the sample in the sample container T or the standard sample in the sample cup C. The sample rack L from which the sample has been aspirated is then moved to the right end position of the transport path 221.

The sample rack L disposed at the right end position of the transport path 221 is pushed to the rack storage section 230 by the forward ( ) Y axis negative direction)movement of a rack pusher 226 The sample rack L that has been moved to the rack storage section 230 is then transported to the forward position of the rack storage section 230 by the rack mover 231.

FIG. 5(a) is a plan view showing the structure of the moving device B disposed below (the side in the Z axis negative direction) the transport path 221 of the rack transporting section 220.

The moving device B is configured by two rack feeders B1 aligned on the Y axis direction. The two rack feeders B1 are configured by an engaging unit B10 capable of engaging the sample rack L, a moving unit B20 for moving the engaging unit B10 in the lateral directions, and transmission type sensors B31 and B32.

The moving unit B20 includes a pulley B21 disposed near the left end of the transport path 221, a pulley B22 disposed near the right end of the transport path 221, a belt B23 looped around the pulleys B21 and B22, a step motor B24 for rotating the pulley B22, and a rotary encoder B25 for outputting a number of pulses corresponding to the amount of rotational displacement of the step motor B24.

The engaging unit B10 is coupled to the belt B23 and configured to move laterally when the the step motor B24 is actuated. The amount of movement of the moving unit B10 is detected by the number of pulses output by the rotary encoder B25. The movement start position and movement end position of the engaging unit B10 are respectively set at the left end and the right end within the drive range of the engaging unit B10. The sensors B31 and B32 respectively detect the engaging unit B10 when the engaging unit B10 is disposed at the movement start position and movement end position.

FIG. 5(b) is a side view showing the essential part of the engaging unit B10.

The engaging unit B10 has engaging members B11 and B12. Engaging hooks B11a and B12a are respectively formed on the engaging members B11 and B12. The engaging members B11 and B12 are movable in vertical directions within the engaging unit B10, and configured to be rotatable within the range of the X-Z planes. The engaging unit B10 engages a guide rail 227 arranged along the X axis direction below (the side in the Z axis negative direction) the transport path 221, so as to be freely oscillatable. The engaging unit B10 moves in lateral directions by means of the guide rail 227 and the moving unit B20.

When the sample rack L is transported laterally on the transport path 221, the engaging members B11 and B12 are first moved to the top side. The engaging hooks B11a and B12a are thus protrude at the top side of the transport path 221 through the channel 221a and 221b of the transport path 221, and are inserted into the concavity L2 of the sample rack L. The engaging members B11 and B12 are then rotated within the X-Z planes to mutually separate the engaging hooks B11a and B12a. As shown in FIG. 5(b), the engaging hooks B11a and B12a therefore engage the concavity of the sample rack L. In this state, the sample rack L can be moved laterally by the movement of the engaging unit B10 in a lateral direction. When the transport of the sample rack L ends, the engaging members B11 and B12 are rotated within the X-Z planes so that the engaging hooks B11a and B12a mutually approach one another. The engaging members B11 and B12 are then moved to the bottom side so that the engaging hooks B11a and B12a are positioned on the bottom side of the transport path 221.

The rack feeder B1 with this engaging unit B10 is arranged in the Y axis direction below the transport path 221 as shown in FIG. 5(a). Hence, two sample racks L can be independently transported laterally in the rack transporting section 220.

Figure 6:
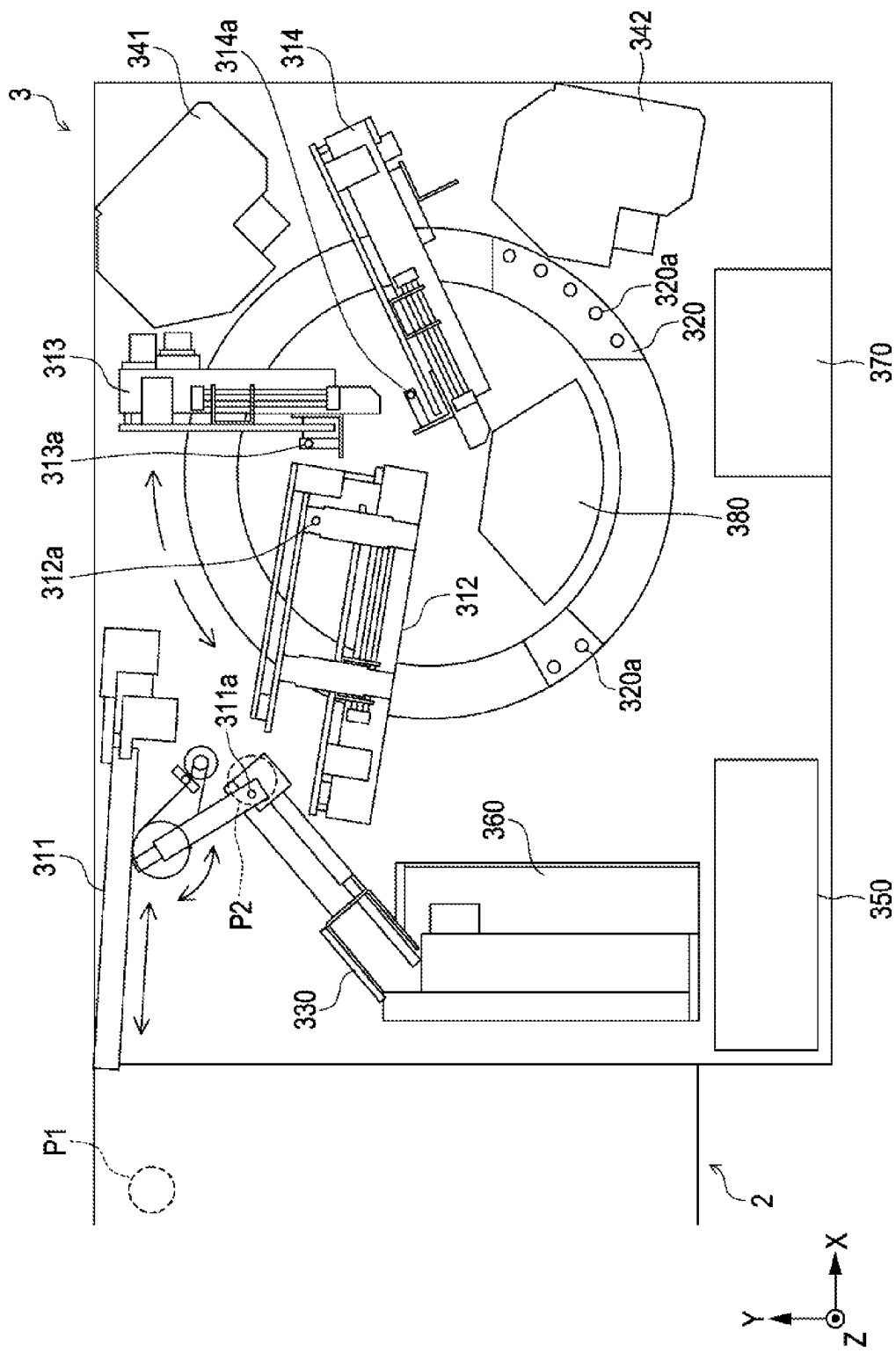
FIG. 6 is a plan view showing the structure of the measurement section of the embodiment viewed from above.

FIG. 6 is a plan view showing the structure when viewing the measurement section 3 from above.

The measurement section 3 has a sample dispensing arm 311, R1 reagent dispensing arm 312, R2 reagent dispensing arm 313, R3 reagent dispensing arm 314, reactor 320, cuvette supplier 330, primary BF (bound free) separation section 341, secondary BF separation section 342, pipette tip supplier 350, detection section 360, R4/R5 reagent supplier 370, and reagent installation section 380.

In the immunoanalyzer 1, the sample of blood, which is the measurement object, is mixed with a buffer solution (R1 reagent), and a reagent (R2 reagent), which contains magnetic particles carrying a capture antibody for binding to the antigen in the sample, is added to the liquid mixture, The magnetic particles carrying the capture antibody bound to the antigen are attracted to a magnet of the primary BF separation section 341, and the component that is not bound to the capture antibody is separated and removed. After a labeled antibody (R3 reagent) has been added, the magnetic particles carrying the capture antibody bound to the antigen and the labeled antibody are attracted to a magnet of the secondary BF separation section 342, and the R3 reagent that contains the unreacted labeled antibody is removed. After adding a luminescent substrate (R5 reagent), which luminesces via reaction between the labeled antibody and a dispersion liquid (R4 reagent), the amount of light produced by the reaction between the labeled antibody and the luminescent substrate is measured. The antigen contained in the sample bound to the labeled antibody can be quantified through this process.

The cuvette supplier 330 is configured to accommodate a plurality of cuvettes, and sequentially supplies the cuvettes one by one to the discharge position P2 of the sample dispensing arm 311.

A pipette 311a for aspirating and discharging R1 reagent is attached to the R1 reagent dispensing arm 312. The R1 reagent dispensing arm 312 aspirates the R1 reagent in the reagent installation section 380 and dispenses (discharges) the aspirated R1 reagent to a cuvette placed at the discharge position P2 via the pipette 312a.

The pipette tip supplier 350 moves a plurality of loaded pipette tips 350a (refer to FIG. 7(a)) one by one to the tip installation position of the sample dispensing arm 311. Thereafter, the pipette tip 350a is mounted on the tip of the pipette 311a of the sample dispensing arm 311 at the tip installation position. The sample dispensing arm 311 uses the mounted pipette tip 350a to aspirate the sample in the sample container T or the standard sample in the sample cup C transported to the aspiration position P1 by the sample transporting section 2.

FIG. 7(a) is a side view showing the vicinity of the pipette 311a of the sample dispensing arm 311. FIG. 7(a) shows the pipette tip 350a mounted on the bottom end (end in the Z axis negative direction) of the pipette 311a.

A sensor 311b for detecting pressure is provided on the inside near the tip of the pipette 311a. The sample dispensing arm 311 also has a syringe 311c for discharging and aspirating the air. The sample dispensing arm 311 is supported by a device for moving the sample dispensing arm 311 in vertical directions (Z axis directions), and the device is moved vertically by a step motor 311d (refer to FIG. 8). The rotary encoder 311e (refer to FIG. 8) outputs a number of pulses corresponding to the rotational displacement of the step motor 311d.

To aspirate the sample or the standard sample disposed at the aspiration position P1, the sample dispensing arm 311 is first moved within the X-Y planes to position the pipette 311a at the aspiration position P1. Then, the sample dispensing arm 311 is lowered by the step motor 311d. At this time air is expelled by the syringe 311c and the air is discharged from the bottom end of the pipette tip 350a. As shown in FIGS. 7(b) and (c), the bottom end of the pipette tip 350a passes through the cap T2 of the sample container T or the cap C1 of the sample cup and touches the sample or the standard sample, and the pressure increase is detected by the sensor 311b. Hence, the liquid surface of the sample or the standard sample aspiration object is detected. When the liquid surface is detected, the lowering of the pipette tip 350a is stopped. The pipette tip 350a is then lowered slightly and a predetermined amount of sample or standard sample is aspirated through the pipette 311a.

Note that since the measurement of the standard sample is substantially the same as the measurement of the sample, the following description focuses on the measurement of the sample.

Returning to FIG. 6, the sample dispensing arm 311 dispenses (discharges) the aspirated sample to the cuvette at the discharge position P2. The R1 reagent was previously dispensed to the cuvette by the R1 reagent dispensing arm 312. Thereafter, the the cuvette is moved to the reactor 320 by a catcher (not shown in the drawing) of the R1 reagent dispensing arm 312.

A pipette 313a for aspirating and discharging R2 reagent is attached to the R2 reagent dispensing arm 313. The R2 reagent dispensing arm 313 aspirates the R2 reagent in the reagent installation section 380 and dispenses (discharges) the aspirated R2 reagent to a cuvette containing the R1 reagent and the sample.

The reactor 320 has an annular shape so as to circumscribe the reagent installation section 380, which is circular, as shown in the drawing. The reactor 320 has a plurality of cuvette holders 320a arranged at equal spacing along the exterior. Cuvettes set in the cuvette holders 320a are heated to approximately 42° C. Hence, the heating promotes reaction of the various reagents and the sample in the cuvette. The reactor 320 is configured to be rotatable in a clockwise direction, and moves the cuvette set in the cuvette holder 320a to each processing position where various processes are performed.

The cuvette containing the sample and R1 and R2 reagents is moved by a catcher (not shown in the drawing) from the reactor 320 to the primary BF separation section 341. The primary BF separation section 341 removes components in the sample which have not become bound to the capture antibody from the sample in the cuvette.

A pipette 314a for aspirating and discharging R3 reagent is attached to the R3 reagent dispensing arm 314. The R3 reagent dispensing arm 314 uses the pipette 314a to aspirate the R3 reagent set at the reagent installation section 380. The R3 reagent dispensing arm 314 also uses the pipette 314a to dispense (discharge) the aspirated R3 reagent into the cuvette which was moved from the primary BF separation section 341 to the reactor 320.

After the elimination process by the primary BF separation section 341, the cuvette containing the R3 reagent and the sample is moved from the reactor 320 to the secondary BF separation section 342 by a catcher (not shown in the drawing). The secondary BF separation section 342 removes the R3 reagent including the unreacted labeled antibody.

The R4/R5 reagent supplier 370 sequentially dispenses R4 and R5 reagents to the cuvette containing the sample after the elimination process performed by the secondary BF separation section 342 via a catcher not shown in the drawing.

The detection section 360 measures the amount of antigen contained in the sample by using a photomultiplier tube to obtain the light generated in the reaction process between the luminescent substrate and the labeled antibody bound to the antigen of the sample which has been subjected to predetermined processing.

Figure 8:
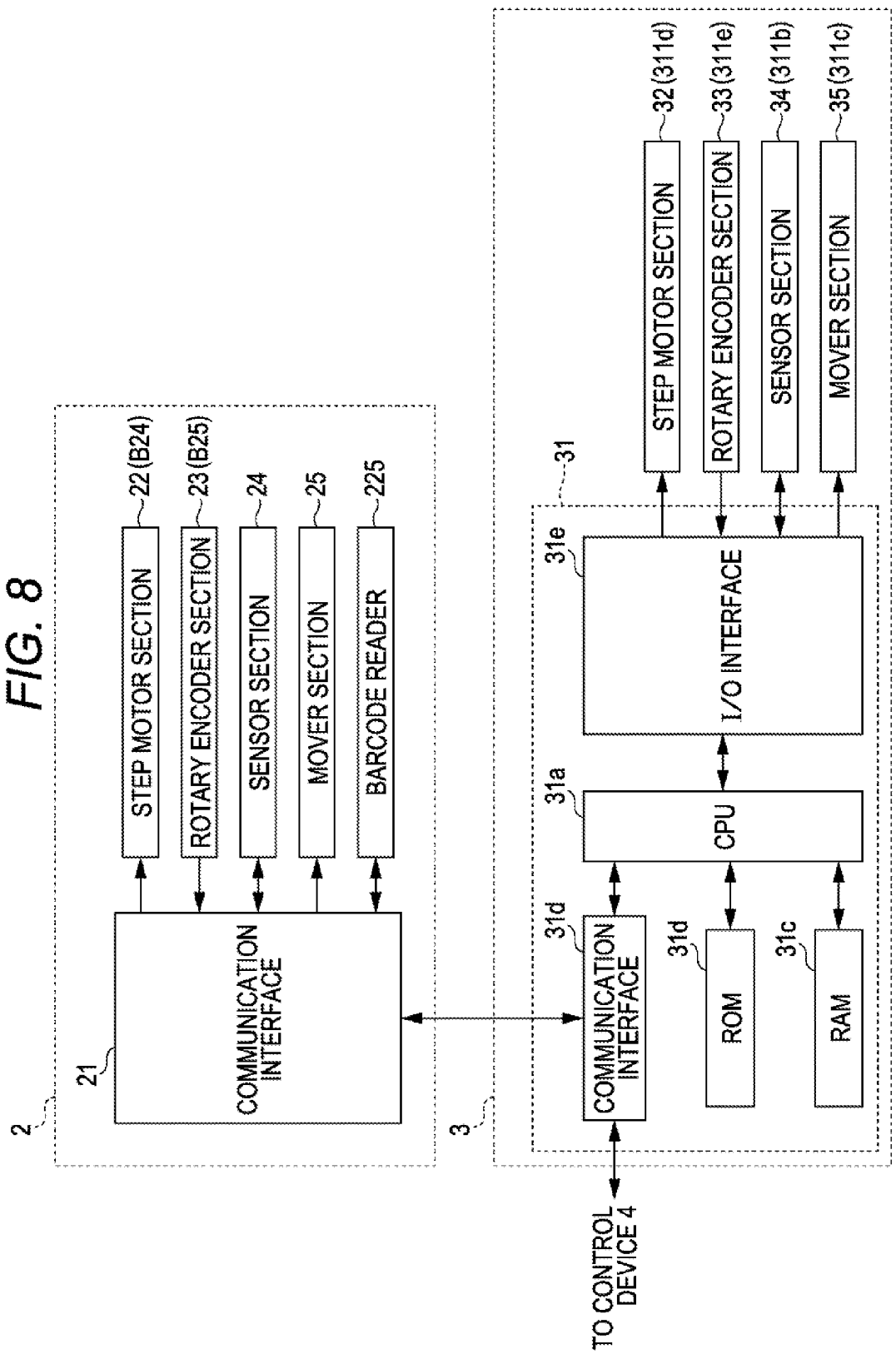
FIG. 8 shows the structures of the sample transporting section and measurement section of the embodiment.

FIG. 8 shows the structures of the sample transporting section 2 and the measurement section 3.

The sample transporting section 2 incorporates a communication interface 21, step motor section 22, rotary encoder section 23, sensor section 24, mover section 25, and barcode reader 225 (refer to FIG. 2).

The communication interface 21 is connected to the measurement section 3 and the various parts within the sample transporting section 2. The step motor section 22 includes two step motors B24 shown in FIG. 5(a), and the rotary encoder section 23 includes two rotary encoders B25 shown in FIG. 5(a). The step motors included in the step motor section 22 are controlled based on the signals received from the measurement section 2 through the communication interface 21. The rotary encoders included in the rotary encoder section 23 output a number of pulses that corresponds to the rotational displacement of the corresponding step motor. The number of pulses output from the rotary encoders included in the rotary encoder section 23 is transmitted to the measurement section 3 through the communication interface 21.

The sensor section 24 incorporates sensors 222a and 222b, sensor 223, sensors 224a and 224b shown in FIG. 2, and sensors B31 and B32 shown in FIG. 5(a), as well as other sensors arranged in the sample transporting section 3. The detection signals of the sensors incorporated in the sensor section 24 are transmitted to the measurement section 3 through the communication interface 21. The mover section 25 incorporates rack feeders 211 and 231 shown in FIG. 2, and a device to drive the rack pushing device 226. The devices included in the mover section 25 are controlled based on the signals received from the measurement section 3 through the communication interface 21.

The bar code reader 225 is controlled based on the signals received from the measurement section 3 through the communication interface 21, and the sample ID and the rack ID read by the barcode reader 225 are transmitted to the measurement section 3 through the communication interface 21.

The measurement section 3 incorporates a controller 31, step motor section 32, rotary encoder section 33, sensor section 34, and mover section 35. The controller 31 includes a CPU 31a, ROM 31b, RAM 31c, communication interface 31d, and I/O interface 31e.

The CPU 31a is capable of executing a computer program stored in the ROM 31b and a computer program loaded in the RAM 31c. The ROM 31b stores the number of pulses output to the step motor B24 to position the sample rack L at a desired position on the transport path 221. The CPU 31a refers to this pulse number and outputs the pulse number needed to the step motor B24 of the sample transporting section 2 to move the sample rack L in a lateral direction to achieve a desired position. Note that the pulse number also may be stored in a battery backup RAM when a writable content battery backup RAM is provided separately from the ROM 31b in the controller 31.

The communication interface 31d is connected to the sample transporting section 2 and the control device 4. The CPU 31a transmits the sample optical information (information of the amount of light produced by the reaction of the labeled antibody and the luminescent substrate)to the control device 4, and receives signals from the control device 4 through the communication interface 31d. The CPU 31a also transmits signals for drive instructions of the sample transporting section 2, and receives signals from the sample transporting section 2 through the communication interface 31d.

The CPU 31a is also connected to the step motor section 32, rotary encoder section 33, sensor section 34, and mover section 35 through the I/O interface 31e.

The step motor section 32 includes a step motor 311d of the sample dispensing arm 311, and the rotary encoder section 33 includes the rotary encoder 311e of the sample dispensing arm 311. The step motor included in the step motor section 32 is controlled by the CPU 31a. The number of pulses output from the rotary encoder included in the rotary encoder section 33 is output to the CPU 31a.

The sensor section 34 includes the sensor 311b shown in FIG. 7. The sensor included in the sensor section 34 is controlled by the CPU 31a, and the detection signals of the sensor included in the sensor section 34 are output to the CPU 31a. The mover section 35 includes the device for driving the syringe section 311c shown in FIG. 7, and the device included in the mover section 35 is controlled by the CPU 31a.

Figure 9:
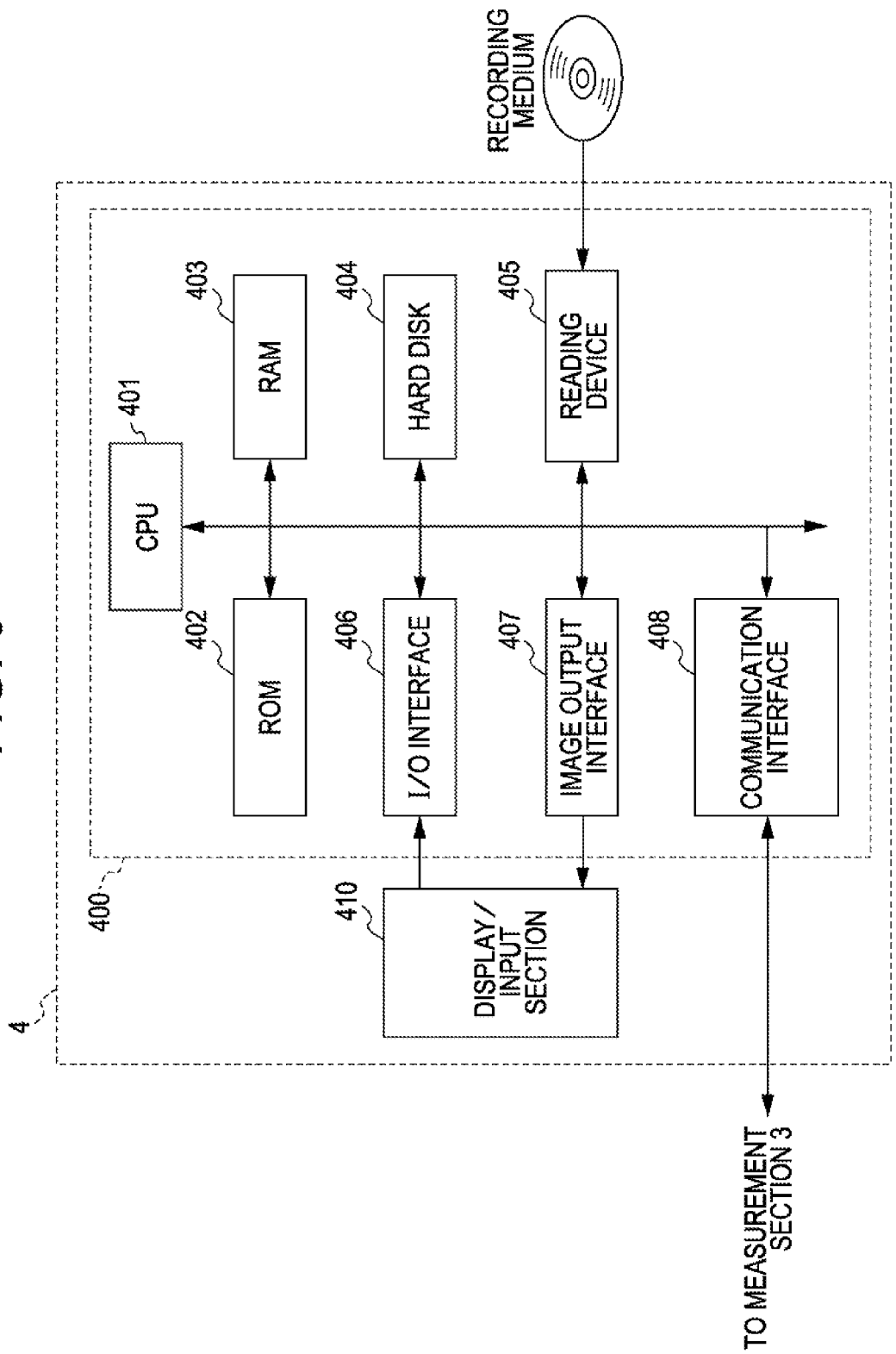
FIG. 9 shows the structures of the control device of the embodiment.

FIG. 9 is a shows the structure of the control device 4.

The control device 4 is configured by a personal computer that includes a main body 400, and display/input part 410. The main body 400 has a CPU 401 ROM 402, RAM 403, hard disk 404, reading device 405, I/O interface 406, image output interface 407, and communication interface 408.

The CPU 401 is capable of executing a computer program stored in the ROM 402 and a computer program loaded in the RAM 403. The RAM 403 is used when reading the computer program stored in the ROM 402 and recorded on the hard disk 404. The RAM 403 is also used as the work area of the CPU 401 when the CPU 401 executes the computer programs.

The hard disk 404 stores an operating system and application programs, as well as the data used when executing the operating system and application programs that are executed by the CPU 401. Specifically, in addition to computer programs and data used for measurements and analysis, the hard disk 404 stores programs for displaying calibration rack setting screen 500 (refer to FIG. 10) and calibration screen 600 (refer to FIG. 11).

The reader 405 is a CD drive or DVD drive capable of reading computer programs and data recorded on a recording medium.

The I/O interface 406 receives the signals output from the display/input section 410. The image output interface 407 outputs image signals corresponding to the image data to the display/input section 410. The display/input section 410 displays images based on the image signals received from the image output interface 407, and outputs instructions received from the user through the screen of the display/input section 410 through the I/O interface 406.

Note that a keyboard image is displayed for receiving input text on the display/input section 410 when test is input via the display/input section 410. The user inputs the test by pressing the letters displayed on the image of the keyboard.

The communication interface 408 transmits signals from the main body 400 to the measurement section 3, and receives signals sent from the measurement section 3.

Figure 10:
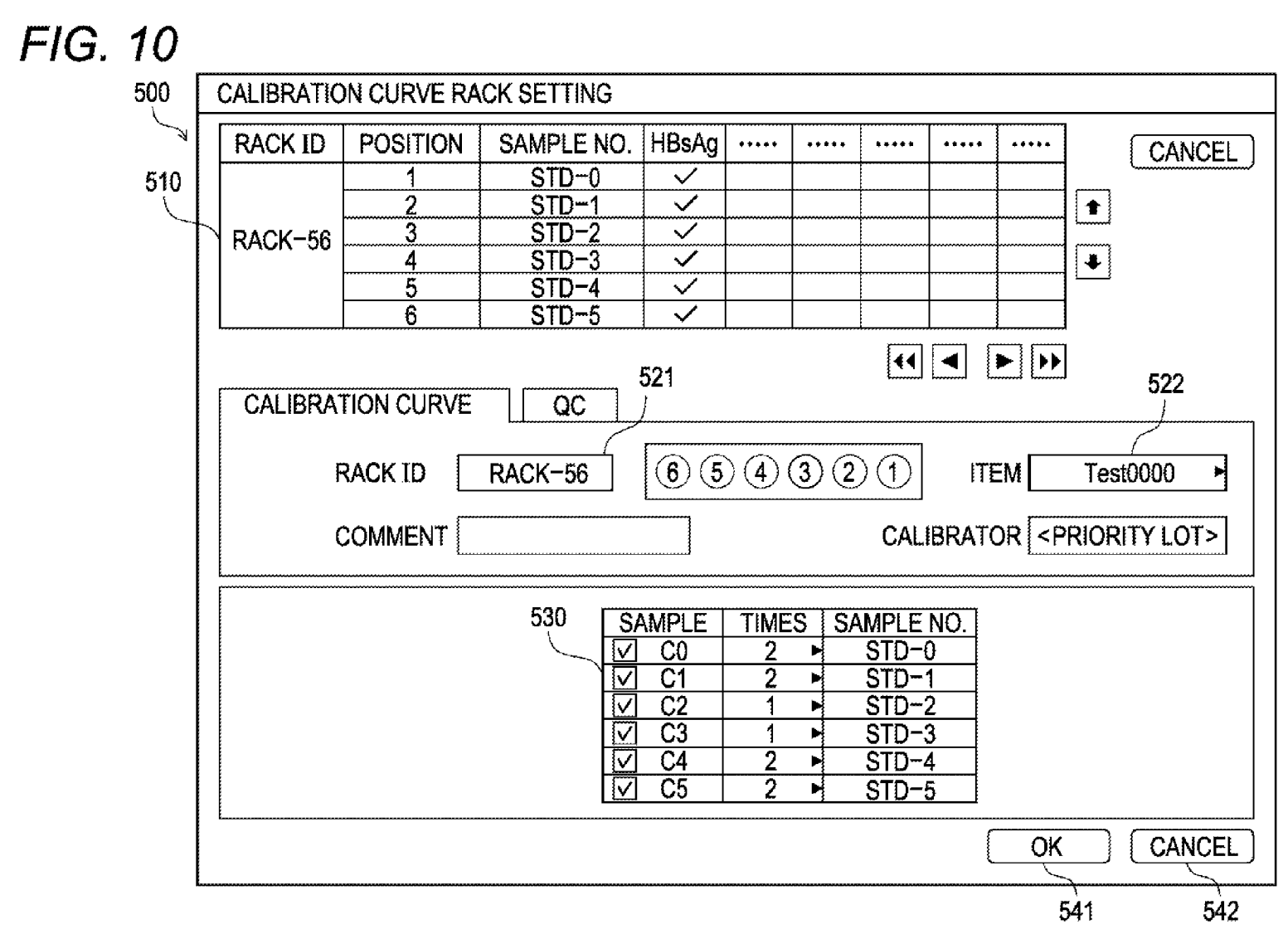

FIG. 10 shows the calibration curve rack setting screen 500 displayed on the display/input section 410 of the control device 4. The calibration curve rack setting screen 500 includes an order list display region 510, input boxes 521 and 522, measurement order display region 530, OK button 541, and cancel button 542.

When a calibration curve is to be prepared, the user loads the sample cups C containing the standard samples in the supporters A01 through A06 of the adapter A mounted on the sample rack L, and records the rack ID of the sample rack L through the calibration curve rack setting screen 500.

The user enters in the input box 521 the rack ID of the sample rack L with the attached adapter A that holds the sample cups C. The input box 522 contains previously recorded and selectable measurement items, and the user operates the input box 522 to enter measurement items. The display of the order list display region 510 and the measurement order display region 530 is performed according to the measurement items selected in the input box 522 and the rack ID input in the input box 521. The user verifies the information related to calibration curve preparation by viewing the content of the displays of the order list display region 510 and the measurement order display region 530.

When the user presses the OK button 541, the information which includes the measurement items and the rack ID of the sample rack L used for calibration curve preparation (hereinafter referred to as "measurement order information") is mutually associated and recorded on the hard disk 404 of the control device 4. When the user presses the cancel button 542, the calibration curve rack setting screen 500 is closed without recording the information on the hard disk 404.

Note that the measurement order containing the associated measurement items and the sample ID of the sample collected from the subject are stored on the hard disk 404 of the control device 4.

FIG. 11 shows the calibration curve screen 600 displayed on the display/input section 410 of the control device 4. The calibration curve screen 600 includes a graph display area 610, validate button 620, and validation display areas 631 and 632.

When performing the measurement of the standard samples in the sample cups C based on the information set in the calibration curve rack setting screen 500, a graph of the prepared calibration curve based on the measurement content is shown in the graph display area 610 as shown in FIG. 11. The user can readily confirm whether the calibration curve is appropriate by referring to the graph of the calibration curve shown in the graph display area 610.

When the user determines that the calibration curve is appropriate, the user presses the validate button 620 to confirm (validate) the calibration curve. When the user performs validation, the validation date is shown in the validation display area 631, and the display content of the validation display area 632 changes from "Not Validated" to "Validated."

The transport process performed by the sample transporting section 2 and the measurement process performed by the measurement section 3 are described below.

The transport process performed by the sample transporting section 2 starts when the user issues a measurement start instruction through the display/input section 410 of the control device 4. Note that in the following description the sample rack L without the attached adapter A is referred to as the "5-sample rack" and the sample rack L with the attached adapter A is referred to as the "6-sample rack," and when neither is specifically differentiated, simply "sample rack L" is used. The 5-sample rack is the normal measurement rack exclusively used for normal measurements of biological samples collected from subjects, and the 6-sample rack is the calibration curve rack used exclusively for measurements of the standard samples for the preparation of the calibration curve.

The processing performed by the CPU 31a of the measurement section 3 is described below with reference to the flow chart of FIG. 12 and the position of the sample rack L on the transport path 221 shown in FIGS. 13(a) through (e) and FIGS. 14(a) through (c).

The CPU 31a of the measurement section 3 determines whether a sample rack L is loaded in the rack set section 210 based on the detection signal of the sensors provided in the rack set section 210 of the sample transporting section 3 (step S101). When a sample rack L is loaded in the rack set section 210 (S101: YES), the CPU 31a drives the rack moving device 211 of the sample transporting section 3 to move the sample rack L to the rack transport part 220 (S102).

The CPU 31a then determines whether the sample rack L is positioned at the left end position of the transport path 221 of the rack transport part 220 via the sensors 222a and 222b. When the sample rack L is positioned at the left end position of the transport path 221 (S103: YES), the CPU 31a determines whether the adapter A is attached to the sample rack L via the sensor 223 (S104). When the adapter A is attached to the sample rack L (S104: YES), the CPU 31a sets "6-sample" as the type of rack (S105). When the adapter A is not attached to the sample rack L (S104: NO), the CPU 31a sets "5-sample" as the type of rack (S106). Note that the rack type (information indicating the type of sample rack L) is stored in the RAM 31c of the measurement section 3.

The CPU 31a then drives the moving device B below the transport path 221 to transport the sample rack L to the right. At this time the barcode reader 225 is positioned at the rack ID reading position, and the sample rack L is transported so that the barcode label L1 is positioned on the front side of the barcode reader 225 as shown in FIGS. 13(a) and 14(a). The barcode reader 225 then reads the rack ID from the barcode label L1 (S107), and the CPU 31a transmits the read rack ID to the control device 4 (S108).

Note that the control device 4 determines whether the rack type of the sample rack L is 5-sample or 6-sample based on the received rack ID in a manner to be described later. The control device 4 transmits the rack type based on the determination result to the measurement section 3.

When the CPU 31a of the measurement section 3 receives the rack type from the control device 4 (S109: YES), the CPU 31a determines whether the rack ID is correct by comparing the rack type set in step S105 or S106 (the rack type determined by the measurement section 3) to the rack type received in S109 (the rack type determined by the control device 4). That is, the rack ID is determined to be incorrect when the rack type determined by the measurement section 3 is 6-sample and the rack type received from the control device 4 is 5-sample. Similarly, the rack ID is determined to be incorrect when the rack type determined by the measurement section 3 is 5-sample and the rack type received from the control device 4 is 6-sample. The rack type is determined to be correct when the rack type determined by the measurement section 3 matches the rack type received from the control device 4.

When the rack ID of the sample rack L is incorrect (S110: YES), the CPU 31a transmits a notice that the rack ID of the sample rack L is incorrect to the control device 4 (S111). Then, the sample rack L is moved to the rack storage section 230 (S112). When the rack ID of the sample rack L is correct (S110: NO), the CPU 31a transmits a notice that the rack ID of the sample rack L is correct to the control device 4 (S113).

When the rack ID is correct, the CPU 31a then determines whether the sample rack L is a 5-sample rack based on the rack type stored in RAM 31c (S114). When the sample rack L is a 5-sample rack (S114: YES), the CPU 31a positions the barcode reader 225 at the position of the supporter L01 at the right end (sample ID reading position). The CPU 31a then drives the barcode reader 225 to read sample ID from the barcode label L1 of the sample container T held by the supporter L01 at the right end (S115).

The CPU 31a then transports the sample rack L a distance d1 to the right as shown in FIG. 13(c) (S116). The CPU 31a repeats the processes of steps S115 through S116 until the reading of the sample IDs is completed for all the sample containers T held by the supporters (S117). Note that the barcode reader 225 skips reading for any supporters that is determined to not hold a sample container T by the sensor 224a. When reading of sample IDs is completed for all sample containers T (S117: YES), the process continues to S118. When the sample rack L is not a 5-sample rack (S114: NO), the process advances to S118.

The CPU 31a then moves the sample rack L to the right to position the supporter L01 at the right end of the sample rack L at the aspiration position P1. That is, when the sample rack L is a 5-sample rack, after all sample IDs of the sample containers T have been read, the sample rack L is positioned with the supporter L01 of the right end disposed at the aspiration position P1 as shown in FIG. 13(d). When the sample rack L is a 6-sample rack, the supporter A01 of the right end is disposed at the aspiration position P1 as shown in FIG. 14(b). The CPU 31a queries the control device 4 to obtain the measurement order information corresponding to the sample ID read in S115, or the measurement order information corresponding to the sample ID read in S107.

The CPU 31a then aspirates the sample from the sample container T held in the supporter A01 at the right end of the sample rack L, or the standard sample from the sample cup C held by the supporter A01 at the right end of the adapter A, and performs measurements of the aspirated sample or standard sample based on the measurement order information obtained from the control device 4. Note that the standard samples are measured in the order of concentration starting with the weakest concentration. The CPU 31a then sequentially transmits the measurement data obtained by these measurements to the control device 4. Note that measurement items are transmitted from the control device 4, and the CPU 31a performs the measurements based on the received measurement items. The measurement operation also may be performed in parallel with the aspiration operation of the next sample or standard sample.

The CPU 31a then determines whether the sample rack L is a 5-sample rack based on the rack type stored in RAM 31c (S119).

When the sample rack L is a 5-sample rack (S119: YES), the CPU 31a moves the sample rack L a distance d1 to the right as shown in FIG. 13(e) (S120). Hence, the second from the right supporter L02 is disposed at the aspiration position P1. The CPU 31a repeats the processes of S118 and S120 until aspiration is completed for all sample containers T held by supporters.

When the sample rack L is a 6-sample rack (S119: NO), the CPU 31a moves the sample rack L a distance d2 to the right as shown in FIG. 14(c) (S121). Hence, the second from the right supporter L02 is disposed at the aspiration position P1. The CPU 31a repeats the processes of S118 and S121 until aspiration is completed for all sample cups C held by supporters (S122).

When aspiration is completed from all sample containers T or sample cups C held by supporters (S122: YES), the sample rack L is transported to the rack storage section 230 (S112). Hence, the processes performed by the measurement section 3 is completed for a single sample rack L.

Figure 15:
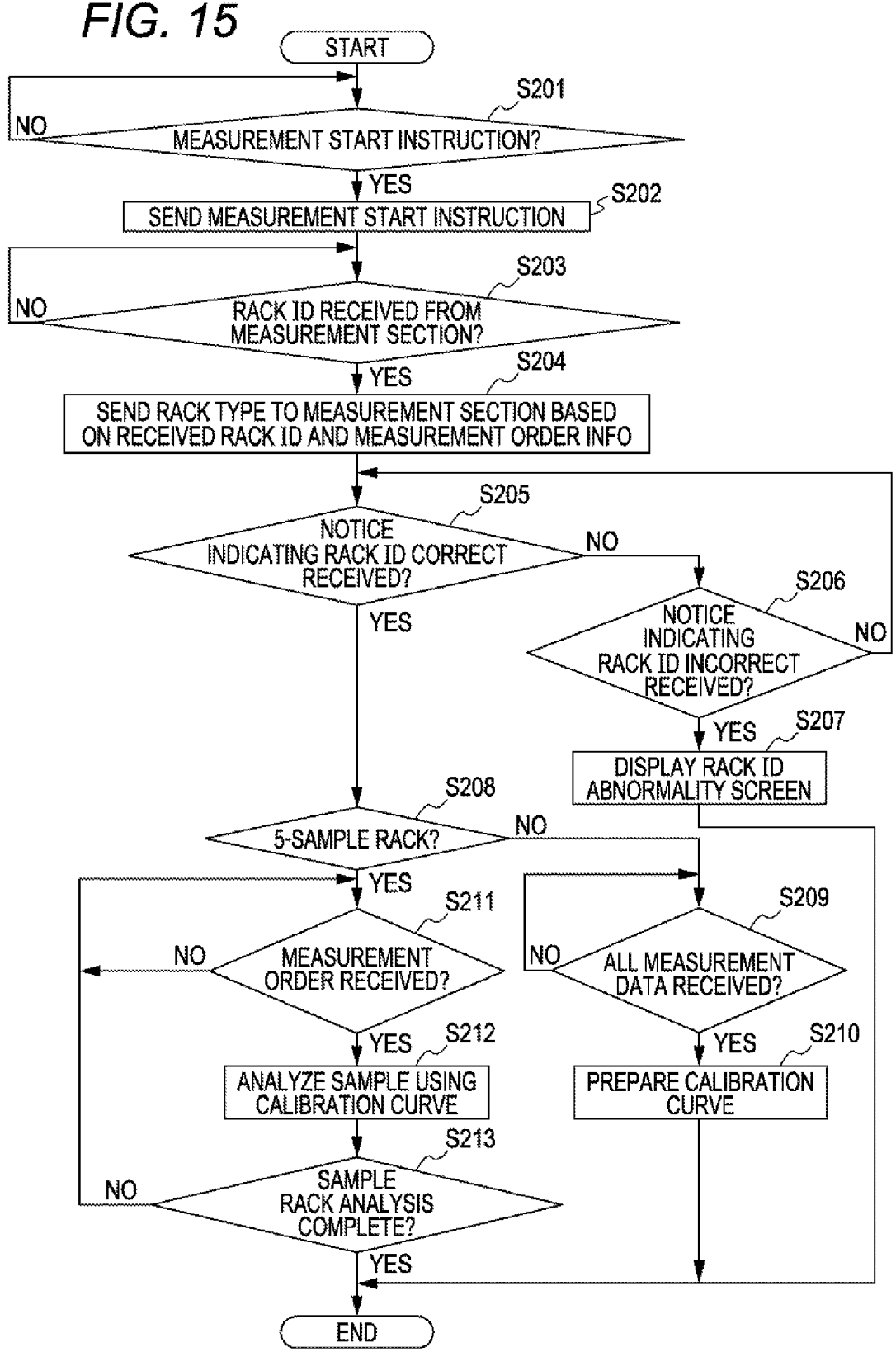
FIG. 15 is a flow chart showing the processing performed by the CPU of the control device of the embodiment.

FIG. 15 is a flow chart showing the processes performed by the CPU 401 of the control device 4.

When the CPU 401 of the control device 4 receives a measurement start instruction from a user through the display/input section 410 (S201: YES), the CPU 401 transmits the measurement start instruction to the measurement section 3 (S202). Hence, the CPU 31a of the measurement section 3 starts the process shown in FIG. 12.

When the rack ID is received from the measurement section 3 in S108 of FIG. 12 (S203: YES), the CPU 401 then transmits the rack type to the measurement section 3 based on the received rack ID and the measurement order information stored on the hard disk 404 (S204). That is, the CPU 401 sets the rack type as 6-sample when the received rack ID includes measurement order information for preparing a calibration curve, and sets the rack type as 5-sample when the received rack ID does not include measurement order information to prepare a calibration curve. The rack type thus set is then transmitted to the measurement section 3.

Note that the rack type transmitted to the measurement section 3 is used to determine whether the rack ID is correct in the measurement section 3, and whether the rack ID is correct is transmitted from the measurement section 3 to the control device 4 in S11 or S113 of FIG. 12.

When a notice that the rack ID is incorrect is received from the measurement section 3 (S205: NO; S206: YES), the CPU 401 then displays the rack ID abnormality screen (refer to FIG. 14(d)) on the display/input section 410, and the process ends.

When a notice indicating the rack ID is correct is received from the measurement section 3 (S205: YES), the CPU 401 determines whether the sample rack L to be aspirated in the measurement section 3 is a 5-sample rack based on the rack type obtained in S204 (S208), and subsequent processing is performed according to the rack type.

When the sample rack L to be aspirated is a 6-sample rack (S208: NO), the CPU 401 receives all the measurement data of the standard samples of the sample rack L from the measurement section 3 (S209: YES) and prepares a calibration curve based on the received measurement data (S210). The prepared calibration curve is stored on the hard disk 404 and shown on the graph display area 610 as shown in FIG. 11. The prepared calibration curve is used for sample analysis when the user confirms (validates) by pressing the validate button 620.

When the sample rack L to be aspirated is a 5-sample rack (S208: YES), the CPU 401 receives the measurement data from the measurement section 3 (S211: YES), and performs sample analysis using the calibration curve prepared in S210 (S212). The CPU 401 performs the processes of S211 through S212 until analysis is completed from all samples in the sample rack L (S213). Note that the sample analysis results are stored on the hard disk 404 and shown on the display/input section 410 according to user display instructions.

According to the present embodiment described above, which provides a a rack exclusively for a calibration curve measurement that can hold a number of containers that is different from the sample rack holding the biological samples of subjects, it is possible to easily make accurate measurement even when the number of standard samples being measures is different than when measuring the biological samples of subjects. For example, when measuring more standard samples than when normally measuring biological samples of subjects, more containers can be held in the rack used exclusively for the calibration curve measurements. Hence, all standard sample containers can be held in a single rack without needing to use two sample racks to hold all the standard containers. This avoids measuring the standard sample sin the wrong order, and allows an accurate calibration curve to be prepared. For example, when preparing a calibration curve using six standard samples, the calibration curve measurements can be made using six sample cups holding the standard samples on a single rack. This prevents measuring the standard samples in the wrong order that may be caused when the sample cups C must be loaded in two or more racks.

According to the above embodiment, it is unnecessary to use a single special rack capable of holding six sample cups C since the adapter A which is configured with six supporters can be attached to a sample rack L configured with only five supporters. The sample rack L with the attached adapter A can be transported using the sample transporting section 2 which has been designed only for transporting the sample rack L without the attached adapter A. Hence, increasing the complexity of the structure of the sample transporting section 2 is avoided.

According to the above embodiment, the length of the sample rack L and the length of the adapter A are identical in the direction aligned with the supporters (longitudinal direction). Hence, the design of the sample transporting section 2 can be simplified since the sample rack L with the attached adapter A can be transported identically to the sample rack L without the attached adapter A.

According to the above embodiment, the spacing d2 of the supporters A01 through A06 is less than the spacing of the supporters L01 through L05. Hence, the number of supporters of the adapter A can be set greater than the number of supporters of the sample rack L even when length of the adapter A and the length of the sample rack L are identical in the direction of alignment of the containers.

According to the above embodiment, the 5-sample rack is sequentially transported a distance d1 to the right when the barcode reader is disposed at the sample ID reading position shown in FIGS. 13(b) and (c). The 5-sample rack is sequentially transported the distance d1 in a rightward direction to position the supporters L01 through L05 at the aspiration position P1 as shown in FIGS. 13(d) and (e). Hence, the sample containers T can be positioned at the sample ID reading position and the aspiration position P1 with high precision. The 6-sample rack is sequentially transported the distance d2 in a rightward direction to position the supporters A01 through A06 at the aspiration position P1 as shown in FIGS. 14(b) and (c). The sample cups C therefore can be positioned at the aspiration position P1 with high precision.

According to the above embodiment, the aspiration of the sample and the standard sample at the aspiration position P1 are performed with similar controls based on the detection of the liquid surface by the sensor 311b. Therefore, when aspirating sample from the sample container T held in the sample rack L, it is not necessary to control to the sample dispensing arm 311 to lower the pipette tip 350a a different amount than when aspirating the standard sample from the sample cup C held in the adapter A. Control of the lowering of the sample dispensing arm 311 is therefore simplified.

According to the above embodiment, when it has been determined that an adapter A is attached to the sample rack L via the sensor 223, but the rack ID read by the barcode reader 225 indicates that this rack L is not a rack for preparing a calibration curve, a rack ID abnormality screen is shown on the display/input section 410 as shown in FIG. 14(d). Similarly, when it has been determined that an adapter A is not attached to the sample rack L via the sensor 223, but the rack ID read by the barcode reader 225 indicates that this rack L is a rack for preparing a calibration curve, the rack ID abnormality screen is also shown on the display/input section 410. The user therefore can reliably prevent unintended measurements.

Although the present invention has been described above by way of an embodiment, the present invention is not limited to this embodiment.

For example, although the above embodiment is described by way of example of blood as an object to be measured, urine also be an object to be measured. That is, the present invention may be applied to an analyzer for analyzing urine, and the invention also may be applied to a clinical examination apparatus for examining other clinical specimens.

A sample rack L with an attached adapter A us used in the above embodiment to support sample cups C containing standard samples for the preparation of a calibration curve. However, the present invention is not limited to this configuration inasmuch as a rack used exclusively for calibration curve measurements having more supporters than the sample rack L may be separately used to support the sample cups C. In this case, the shape of the rack used exclusively for calibration curve measurements is preferably the same shape as the sample rack L (for example, has the same widths in the longitudinal direction and latitudinal direction as the sample rack L). Hence, the rack used exclusively for calibration curve measurements can be transported the same as when transporting the sample rack L within the sample transporting section 2.

Although the sample rack L (the rack used for usual measurements) has 5 supporters in the above embodiment, the number of supporters of the sample rack L may be other than 5 (for example, 10). Although the supporters of the adapter A (the rack used exclusively for calibration measurements) in the above embodiment has one more supporter than the sample rack L, the present invention is not limited to this configuration inasmuch as the adapter A may have two or more supporters than the sample rack L. Note that the number of supporters of the adapter A (that is, supporters of the rack used exclusively for calibration measurements) preferably matches the number of standard samples needed to prepare an appropriate calibration curve. Accurate calibration curve measurements can be executed more easily without empty supporters in the adapter A.

Although supporters of the adapter A (that is, the rack used exclusively for calibration curve measurements) are more numerous than the supporters of the sample rack L (the rack used for usual measurements) in the above embodiment, the number of supporters of the adapter A also may be fewer than the the number of supporters of the sample rack L. Note that the number of supporters of the adapter A preferably matches the number of standard samples needed to prepare an appropriate calibration curve. Accurate calibration curve measurements can be executed more easily without empty supporters in the adapter A.

Barcode labels T1 and L1 are respectively adhered to the sample container T and the sample rack L in the above embodiment to discriminate the sample containers T and the sample racks L; however, the present invention is not limited to this configuration inasmuch as RFIDs (radio frequency identification) also may be adhered. When an RFID is adhered, an antenna is provided in the sample transporting section 2 to obtain the information from the RFID instead of the barcode reader 225.

Although detection of the liquid surface is performed by the sensor 311b when aspirating the sample and standard sample at the aspiration position P1 in the above embodiment, the present invention is not limited to this configuration since the bottom end of the pipette tip 350a near or in contact with the liquid surface also may be detected by another detection means such as an capacitance sensor. Furthermore, the pipette tip 350a also may be lowered by an amount that has been previously set without detecting the liquid surface. That is, the bottom end of the pipette tip 350a may be lowered to near the bottom surface of the sample container T when aspirating a sample, and the bottom end of the pipette tip 350a may be lowered to near the bottom of the sample cup C when aspirating standard sample.

Although the display/input section 410 of the above embodiment is configured as a touch panel used for both display and input, the present invention is not limited to this arrangement inasmuch as a display unit and an input unit may be provided separate.

Although the sensor 223 is configured as a lever-type sensor in the above embodiment, the invention is not limited to this configuration since a light shield-type or reflective type sensor also may be used.

In the above embodiment, a rack abnormality screen shown in FIG. 14(d) is shown on the display/input section 410 when the CPU 401 of the control device 4 receives a notice that the rack ID is incorrect (S201: YES). However, the present invention is not limited to this configuration since the CPU 401 may issue an audible sound informing the user of an abnormality from a speaker provided in the control device 4 instead of, or together with the showing the rack abnormality screen. When the CPU 31a of the measuring section 3 transmits a notice that the rack ID is incorrect to the control device 4 (S111), a screen indicating an abnormality may be shown on a display provided in the measurement section 3, or an audible warning of the abnormality may be issued from a speaker provided in the measurement section 3.

Although the CPU 31a of the measurement section 3 controls the sample transporting section 2 in the above embodiment, the invention is not limited to this configuration since the control device 4 also may control the sample transporting section 2. Moreover, the controller 31 may be omitted and the control device 4 may perform the controls of the sample transporting section 2 and the measurement section 3.

Note that the present invention is not limited to the above described embodiments and may be variously modified insofar as such modification are within the scope of the claims.

What is claimed is:

1. A sample analyzer, comprising:
a first rack which includes a first number of supporters for supporting containers that contain biological samples of subjects;
a second rack which includes a second number of supporters for supporting containers that contain standard samples, wherein the second number of supporters is different from the first number of supporters;
a transporting section, including at least one motor, a pulley, a transport path, a rotary encoder and a belt, configured to transport the first rack, and configured to transport the second rack;
an information obtaining section, outside of the transporting section, which comprises at least one of a barcode reader and an antenna and is configured to obtain rack identification information indicating the first rack or the second rack from a first recording part affixed on a rack transported by the transporting section;
a memory configured to store the rack identification information indicating the second rack in association with a measurement item;
a measurement section, outside of the transporting section and comprising a reactor and separation sections, configured to measure a sample in one of the containers, transported by the transporting section, by using at least an optical detector to analyze amounts of light produced by a first reaction in the container and a second reaction in another container, and
a controller configured to determine, by a value of rack identification information sensed by at least a sensor located in the transporting section, whether the rack transported by the transporting section is the first rack or the second rack based on the obtained rack identification information in the information obtaining section; the controller is further configured, when it has been determined that the rack transported by the transporting section is the second rack based on the obtained rack identification information, to control the transporting section to perform a transporting operation according to the second rack and control the measurement section to perform the measurement of the standard samples in the containers supported by the second rack in a predetermined order for preparing a calibration curve based on the measurement item associated with the rack identification information; and the controller is also further configured to prepare the calibration curve used for analyzing a measurement result of a biological sample, by plotting points of the calibration curve according to the amounts of light detected by the optical detector linked to the controller, wherein
the second rack is the first rack with an attached adapter having the second number of supporters for supporting containers;
the sample analyzer further comprises a detector configured to detect a rack with the attached adapter; and
the controller is further configured to execute a process to issue a warning when the information obtaining section has obtained identification information of the first rack and the detector has detected the rack with the attached adapter, and
the controller is also further configured to determine that the rack transported by the transporting section is the second rack through use of the detector which is linked to the controller.

2. The sample analyzer of claim 1, further comprising:
a display on an outside of the sample analyzer; and
an input section of the display, wherein
the display shows an order entry screen which has a first input field for inputting, via the input section, rack identification information indicating the second rack, and a second input field for inputting, via the input section, a measurement item; and
the memory stores the rack identification information input in the first input field in association with the measurement item input in the second input field.

3. A sample analyzer, comprising:
a first rack which includes a first number of supporters for supporting containers that contain biological samples of subjects;
a second rack which includes a second number of supporters for supporting containers that contain standard samples, wherein the second number of supporters is different from the first number of supporters;

a transporting section, including at least one motor, a pulley, a transport path, a rotary encoder and a belt, configured to transport the first rack, and configured to transport the second rack;

a measurement section, outside of the transporting section and including a reactor and separation sections, configured to measure a sample in one of the containers, transported by the transporting section, by using at least an optical detector to analyze amounts of light produced by a first reaction in the container and a second reaction in another container, and a controller configured to determine., by a value of rack identification information sensed by at least one sensor located in the transporting section, whether a rack transported by the transporting section is the first rack or the second rack; the controller is further configured, when it has been determined that the rack transported by the transporting section is the second rack, to control the transporting section to perform a transporting operation according to the second rack and control the measurement section measure the standard samples in the containers supported by the second rack in a predetermined order; and the controller is also further configured to prepare a calibration curve used for analyzing a measurement result of a biological sample, by plotting points of the calibration curve according to the amounts of light detected by the optical detector linked to the controller, wherein the second rack is the first rack with an attached adapter having the second number of supporters for supporting containers;

the sample analyzer further comprises a detector configured to detect a rack with the attached adapter; and the controller is further configured to determine that a rack transported by the transporting section is the second rack when the detector has detected the rack with the attached adapter, wherein the controller is also further configured to determine that the rack transported by the transporting section is the second rack through use of the detector which is linked to the controller.

4. The analyzer of claim 3, wherein
the adapter is attached above the supporters of the first rack.

5. The analyzer of claim 4, wherein
the plurality of supporters of the first rack are formed at intervals of a first spacing; and
the plurality of supporters of the adapter are formed at intervals of a second spacing that is different from the first spacing.

6. The analyzer of claim 5, wherein
the transport path transports the first rack toward a predetermined position:
the measurement section is configured to measure the sample in the container located at the predetermined position;
the controller is configured to:
control the transporting section to move the first rack along the transport path toward the predetermined position a first distance according to the first spacing so that the container supported by the first rack is located at the predetermined position, when the transporting section transports the first rack; and
control the transporting section to move the second rack along the transport path toward the predetermined position a second distance according to the second spacing so that the container supported by the adapter of the second rack is located at the predetermined position, when the transporting section transports the second rack.

7. The analyzer of claim 6, wherein
when viewed from above with the adapter attached to the first rack, the supporter positioned at a head of the first rack and the supporter disposed at a head of the adapter are aligned at a sample position;
the controller is configured to:
control the transporting section to move the first rack toward the predetermined position the first distance after moving the supporter at the head of the first rack to the predetermined position so that the container supported by a next supporter adjacent to the head supporter is located at the predetermined position when the transporting section transports the first rack; and
control the transporting section to move the second rack toward the predetermined position the second distance after moving the supporter at the head of the adapter to the predetermined position so that the container supported by a next supporter adjacent to the head supporter is located at the predetermined position when the transporting section transports the second rack.

8. The analyzer of claim 7, wherein
when viewed from above, a distance from the supporter positioned at the head of the first rack to a front end of the first rack, and a distance from the supporter positioned at the head of the adapter to a front end of the adapter are identical.

9. The analyzer of claim 7, wherein
when viewed from above with the adapter attached to the first rack, the supporter positioned at a rearmost position of the first rack and the supporter at a rearmost position of the adapter are aligned at a sample position.

10. The sample analyzer of claim 1, further comprising:
an aspirating section which comprises an aspirating tube and a liquid surface sensor for detecting a liquid surface, and which aspirates a liquid in a container by inserting the aspirating tube into a container, wherein
when aspirating the liquid from the container, the aspirating section lowers the aspirating tube into the container and stops lowering the aspirating tube based on the detection of the liquid surface by the liquid surface sensor.

11. A sample analyzer, comprising:
a first rack which includes a first number of supporters for supporting containers that contain biological samples of subjects;
a second rack which includes a second number of supporters for supporting containers that contain standard samples, wherein the second number of supporters is different from the first number of supporters;
a transporting section, including at least one motor, a pulley, a transport path, a rotary encoder and a belt, configured to transport the first rack, and configured to transport the second rack;
a measurement section, outside of the transporting section and comprising a reactor and separation sections, configured to measure a sample in one of the containers, transported by the transporting section, by using at least an optical detector to analyze amounts of light produced by a first reaction in the container and a second reaction in another container, and
a controller configured to determine, by a value of rack identification information sensed by at least one sensor located in the transporting section, whether a rack transported by the transporting section is the first rack or the second rack; the controller is further configured, when it has been determined that the rack transported by the transporting section is the second rack, to control the transporting section to perform a transporting operation according to the second rack and control the measurement section to measure the standard samples in the containers supported by the second rack in a predetermined order; and the controller is also further configured to prepare a calibration curve used for analyzing a measurement result of a biological sample, by plotting points of the calibration curve according to the amounts of light detected by the optical detector linked to the controller, wherein the second rack has a length that is identical to that of the first rack in an alignment direction of the containers, wherein the controller is further configured to determine that the rack transported by the transporting section is the second rack through use of a detector which is linked to the controller.

12. The analyzer of claim 1, wherein
the memory stores measurement items in association with sample identification information for identifying the biological samples supported by the first rack;
a second recording part recording the sample identification information is affixed on each container supported by the first rack; and
based on at least a value sensed by a sensor, when the information obtaining section has obtained rack identification information indicating the first rack and communicates the rack identification information to the controller, the controller is further configured to control the transporting section, via first electrical signals communicated along a first link from the controller to the transporting section, to perform a transport operation according to the first rack, to control, by outputting a first control signal to the information obtaining section, the information obtaining section to obtain sample identification information from the second recording part of each container supported by the first rack transported by the transporting section, and to control, by outputting a second control signal to the measurement section, the measurement section, via second electrical signals communicated along a second link from the controller to the measurement section, to execute measurement of the biological sample in each container supported by the first rack based on a measurement item associated with the sample identification information obtained by the information obtaining section.

13. The analyzer of claim 1, wherein
the controller is further figured to control the measurement section to measure the standard samples in the containers in the second rack in an order of concentration.

14. The analyzer of claim 1, wherein
the second number is the number of containers required to prepare a calibration curve.

15. The analyzer if claim 1, wherein
the second number is greater than the first number.

16. A method for controlling a sample analyzer that comprises a first rack which includes a first number of supporters for supporting containers that contain biological samples of subjects, a second rack which includes a second number of supporters for supporting containers that contain standard samples, the second number of supporters is different from the first number of supporters, a transporting section, including at least one motor, a pulley, a transport path, a rotary encoder and a belt, for transporting a rack and a measurement section for measuring a sample in one of the containers supported by the rack, the method comprising steps of:

determining, by a value of rack identification sensed by at least one sensor located in the transporting section, whether a transport object of the transporting section is the first rack, or the second rack;

controlling the transporting section to perform a transport operation according to the second rack when the transport object has been determined to be the second rack;

controlling the measurement section, comprising a reactor and separation sections, to measure, by using at least an optical detector to analyze amounts of light produced by reactions in the containers, in a predetermined order, the standard samples in the containers supported by the second rack transported by the transporting section; and preparing a calibration curve used in an analysis of a measurement result of a biological sample by plotting points of the calibration curve according to the amounts of light detected by the optical detector linked to the controller, wherein the second rack is the first rack with an attached adapter having the second number of supporters for supporting containers;

the method further comprises a step of detecting a rack with the attached adapter; and the transport object is determined to be the second rack when the rack with the attached adapter has been detected, wherein the determining whether that a rack transported by the transporting section is the second rack is determined through use of a detector which is linked to a controller.

* * * * *